US009605310B2

(12) United States Patent
Balasubramanian et al.

(10) Patent No.: US 9,605,310 B2
(45) Date of Patent: **\*Mar. 28, 2017**

(54) LABELLED NUCLEOTIDES

(71) Applicant: Illumina Cambridge Limited, Nr. Saffron Walden, Essex (GB)

(72) Inventors: Shankar Balasubramanian, Cambridge (GB); Colin Barnes, Nr. Saffron Walden (GB); Xiaohai Liu, Nr. Safron Walden (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,566

(22) Filed: Aug. 7, 2015

(65) Prior Publication Data

US 2016/0060692 A1   Mar. 3, 2016

Related U.S. Application Data

(60) Continuation of application No. 14/094,646, filed on Dec. 2, 2013, now Pat. No. 9,121,062, which is a continuation of application No. 13/437,772, filed on Apr. 2, 2012, now abandoned, which is a continuation of application No. 12/804,025, filed on Jul. 13, 2010, now Pat. No. 8,158,346, which is a division of application No. 12/283,285, filed on Sep. 9, 2008, now Pat. No. 7,772,384, which is a continuation of application No. 10/497,594, filed as application No. PCT/GB02/05474 on Dec. 4, 2002, now Pat. No. 7,427,673, which is a continuation-in-part of application No. 10/227,131, filed on Aug. 23, 2002, now Pat. No. 7,057,026.

(30) Foreign Application Priority Data

Dec. 4, 2001   (GB) .................................. 0129012.1

(51) Int. Cl.
| | | |
|---|---|---|
| *C12Q 1/68* | (2006.01) | |
| *C12P 19/34* | (2006.01) | |
| *C07H 19/10* | (2006.01) | |
| *C07H 19/20* | (2006.01) | |
| *C07H 21/00* | (2006.01) | |

(52) U.S. Cl.
CPC ........... *C12Q 1/6869* (2013.01); *C07H 19/10* (2013.01); *C07H 19/20* (2013.01); *C07H 21/00* (2013.01); *C12P 19/34* (2013.01); *C12Q 1/6874* (2013.01); *C12Q 1/6876* (2013.01); *C12Q 2525/186* (2013.01)

(58) Field of Classification Search
CPC .................................................... C12Q 1/6869
USPC ...................................... 435/6.1, 91.1, 91.2
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,824,775 A | 4/1989 | Dattagupta et al. |
| 4,863,849 A | 9/1989 | Melamede |
| 4,888,274 A | 12/1989 | Radding et al. |
| 5,047,519 A | 9/1991 | Hobbs, Jr. et al. |
| 5,118,605 A | 6/1992 | Urdea |
| 5,174,962 A | 12/1992 | Brennan et al. |
| 5,175,269 A | 12/1992 | Stavrianopoulos |
| 5,242,796 A | 9/1993 | Prober et al. |
| 5,302,509 A | 4/1994 | Cheeseman |
| 5,328,824 A | 7/1994 | Ward et al. |
| 5,436,143 A | 7/1995 | Hyman |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen |
| 5,547,839 A | 8/1996 | Dower et al. |
| 5,547,859 A | 8/1996 | Goodman et al. |
| 5,602,000 A | 2/1997 | Hyman |
| 5,712,378 A | 1/1998 | Wang |
| 5,763,594 A | 6/1998 | Hiatt et al. |
| 5,770,367 A | 6/1998 | Southern et al. |
| 5,798,210 A | 8/1998 | Canard et al. |
| 5,808,045 A | 9/1998 | Hiatt et al. |
| 5,821,356 A | 10/1998 | Khan et al. |
| 5,849,542 A | 12/1998 | Reeve et al. |
| 5,872,244 A | 2/1999 | Hiatt et al. |
| 5,885,775 A | 3/1999 | Haff et al. |
| 5,959,089 A | 9/1999 | Hannessian |
| 6,001,566 A | 12/1999 | Canard et al. |
| 6,008,379 A | 12/1999 | Benson et al. |
| 6,013,445 A | 1/2000 | Albrecht |
| 6,046,005 A | 4/2000 | Ju et al. |
| 6,074,823 A | 6/2000 | Koster |
| 6,087,095 A | 7/2000 | Rosenthal et al. |
| 6,136,543 A | 10/2000 | Anazawa et al. |
| 6,214,987 B1 | 4/2001 | Hiatt et al. |

(Continued)

FOREIGN PATENT DOCUMENTS

| | | |
|---|---|---|
| DE | 4141178 | 6/1993 |
| EP | 251786 | 11/1994 |

(Continued)

OTHER PUBLICATIONS

U.S. Appl. No. 13/316,204, filed Dec. 9, 2011, Liu et al.

(Continued)

*Primary Examiner* — Jezia Riley
(74) *Attorney, Agent, or Firm* — Jones Day

(57) ABSTRACT

Nucleosides and nucleotides are disclosed that are linked to detectable labels via a cleavable linker group.

16 Claims, 6 Drawing Sheets

(56) References Cited

U.S. PATENT DOCUMENTS

| | | |
|---|---|---|
| 6,218,118 B1 | 4/2001 | Sampson et al. |
| 6,218,530 B1 | 4/2001 | Rothschild et al. |
| 6,232,465 B1 | 5/2001 | Hiatt et al. |
| 6,242,193 B1 | 6/2001 | Anazawa et al. |
| 6,255,083 B1 | 7/2001 | Williams |
| 6,255,475 B1 | 7/2001 | Kwiatkowski |
| 6,287,821 B1 | 9/2001 | Shi et al. |
| 6,309,836 B1 | 10/2001 | Kwiatkowski |
| 6,310,189 B1 | 10/2001 | Fodor et al. |
| 6,312,893 B1 | 11/2001 | Van Ness et al. |
| 6,335,155 B1 | 1/2002 | Wells et al. |
| 6,380,378 B1 | 4/2002 | Kitamura et al. |
| 6,485,944 B1 | 11/2002 | Church et al. |
| 6,524,829 B1 | 2/2003 | Seeger |
| 6,613,508 B1 | 9/2003 | Van Ness et al. |
| 6,613,523 B2 | 9/2003 | Fischer |
| 6,639,088 B2 | 10/2003 | Kwiatkowski |
| 6,664,079 B2 | 12/2003 | Ju et al. |
| 6,780,591 B2 | 8/2004 | Williams et al. |
| 6,787,308 B2 | 9/2004 | Balasubramanian et al. |
| 6,911,345 B2 | 6/2005 | Quake et al. |
| 6,982,146 B1 | 1/2006 | Schneider et al. |
| 7,037,654 B2 | 5/2006 | Chenna et al. |
| 7,037,687 B2 | 5/2006 | Williams et al. |
| 7,056,666 B2 | 6/2006 | Dower et al. |
| 7,057,026 B2 | 6/2006 | Barnes et al. |
| 7,057,031 B2 | 6/2006 | Olenjnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,279,563 B2 | 10/2007 | Kwiatkowski |
| 7,345,159 B2 | 3/2008 | Ju et al. |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,771,973 B2 | 8/2010 | Milton et al. |
| 7,772,384 B2 | 8/2010 | Balasubramanian et al. |
| 7,785,790 B1 | 8/2010 | Church et al. |
| 7,785,796 B2 | 8/2010 | Balasubramanian et al. |
| 7,795,424 B2 | 9/2010 | Liu et al. |
| 7,816,503 B2 | 10/2010 | Milton et al. |
| 8,071,739 B2 | 12/2011 | Milton et al. |
| 8,084,590 B2 | 12/2011 | Liu et al. |
| 8,148,064 B2 | 4/2012 | Balasubramanian et al. |
| 8,158,346 B2 | 4/2012 | Balasubramanian et al. |
| 8,394,586 B2 | 3/2013 | Balasubramanian et al. |
| 9,121,060 B2 | 9/2015 | Milton et al. |
| 2003/0008285 A1 | 1/2003 | Fischer |
| 2003/0104437 A1 | 6/2003 | Barnes et al. |
| 2003/0186256 A1 | 10/2003 | Fischer |
| 2004/0014096 A1 | 1/2004 | Anderson et al. |
| 2004/0039189 A1 | 2/2004 | Guimil et al. |
| 2004/0096825 A1 | 5/2004 | Chenna et al. |
| 2006/0160081 A1 | 7/2006 | Milton et al. |
| 2006/0188901 A1 | 8/2006 | Barnes et al. |
| 2007/0166705 A1 | 7/2007 | Milton et al. |
| 2010/0159531 A1 | 6/2010 | Gordon et al. |
| 2010/0292452 A1 | 11/2010 | Milton et al. |
| 2010/0317531 A1 | 12/2010 | Balasubramanian et al. |
| 2010/0323350 A1 | 12/2010 | Gordon |
| 2011/0020827 A1 | 1/2011 | Milton et al. |
| 2011/0124054 A1 | 5/2011 | Olejnik et al. |
| 2011/0183327 A1 | 7/2011 | Balasubramanian et al. |
| 2012/0052489 A1 | 3/2012 | Gordon et al. |
| 2012/0095201 A1 | 4/2012 | Milton et al. |
| 2012/0156671 A1 | 6/2012 | Liu et al. |
| 2012/0202196 A1 | 8/2012 | Balasubramanian et al. |
| 2012/0252010 A1 | 10/2012 | Balasubramanian et al. |
| 2013/0189743 A1 | 7/2013 | Balasubramanian et al. |

FOREIGN PATENT DOCUMENTS

| | | |
|---|---|---|
| EP | 0992511 | 4/2000 |
| EP | 1182267 | 2/2002 |
| EP | 1291354 | 3/2003 |
| EP | 0808320 | 4/2003 |
| EP | 2325304 | 9/2004 |
| EP | 1730307 | 12/2006 |
| EP | 1337541 | 3/2007 |
| EP | 1218391 | 4/2007 |
| EP | 1790736 | 5/2007 |
| EP | 1560838 | 5/2009 |
| EP | 2119722 | 11/2009 |
| EP | 2338893 | 6/2011 |
| WO | WO 8909282 | 10/1989 |
| WO | WO 8910977 | 11/1989 |
| WO | WO 9013666 | 11/1990 |
| WO | WO 9106678 | 5/1991 |
| WO | WO 9210587 | 6/1992 |
| WO | WO 9305183 | 3/1993 |
| WO | WO 9321340 | 10/1993 |
| WO | WO 9414972 | 7/1994 |
| WO | WO 9607669 | 3/1996 |
| WO | WO 9611937 | 4/1996 |
| WO | WO 9623807 | 8/1996 |
| WO | WO 9627025 | 9/1996 |
| WO | WO 9830720 | 7/1998 |
| WO | WO 9833939 | 8/1998 |
| WO | WO 9905315 | 2/1999 |
| WO | WO 9949082 | 9/1999 |
| WO | WO 9957321 | 11/1999 |
| WO | WO 0002895 | 1/2000 |
| WO | WO 0006770 | 2/2000 |
| WO | WO 0015844 | 3/2000 |
| WO | WO 0018956 | 4/2000 |
| WO | WO 0021974 | 4/2000 |
| WO | WO 0050642 | 8/2000 |
| WO | WO 0053805 | 9/2000 |
| WO | WO 0053812 | 9/2000 |
| WO | WO 0070073 | 11/2000 |
| WO | WO 0116375 | 3/2001 |
| WO | WO 0123610 | 4/2001 |
| WO | WO 0125247 | 4/2001 |
| WO | WO 0132930 | 5/2001 |
| WO | WO 0157248 | 8/2001 |
| WO | WO 0157249 | 8/2001 |
| WO | WO 0192284 | 12/2001 |
| WO | WO 0202813 | 1/2002 |
| WO | WO 0222883 | 3/2002 |
| WO | WO 0229003 | 4/2002 |
| WO | WO 02072892 | 9/2002 |
| WO | WO 02079519 | 10/2002 |
| WO | WO 02088381 | 11/2002 |
| WO | WO 02088382 | 11/2002 |
| WO | WO 03002767 | 1/2003 |
| WO | WO 03020968 | 3/2003 |
| WO | WO 03048178 | 6/2003 |
| WO | WO 03048387 | 10/2003 |
| WO | WO 03085135 | 10/2003 |
| WO | WO 2004007773 | 1/2004 |
| WO | WO 2004018493 | 3/2004 |
| WO | WO 2004018497 | 3/2004 |
| WO | WO 2005084367 | 9/2005 |

OTHER PUBLICATIONS

U.S. Appl. No. 13/432,989, filed Mar. 28, 2012, Balasubramanian et al.

U.S. Appl. No. 90/008,149, filed Aug. 3, 2006, Hiatt et al., reexam requested by Gitten.

U.S. Appl. No. 90/008,152, filed Aug. 3, 2006, Hiatt et al., reexam requested by Gitten.

"Gene Characterization Kits", p. 39, Stratagene Catalog (1988).

Beckman Coulter CEQ(TM) 2000 DNA Analysis System User's Guide, 606913-AC, dated Jun. 2000.

Bergmann, et al., "Allyl as Internucleotide Protecting Group in DNA Synthesis to be Cleaved Off by Ammonia", Tetrahedron, 51(25):6971-6976 (1995).

(56) References Cited

OTHER PUBLICATIONS

Brunckova, et al., "Intramolecular Hydrogen Atom Abstraction in Carbohydrates and Nucleosides: Inversion of an α- to β-Manopyranoside and Generation of Thymidine C-4' Radicals", Tetrahedron Letters 35:6619-6622 (1994).
Burgess, et al., "An Approach to Photolabile, Fluorescent Protecting Groups", J. Org. Chem., 62:5165-5168 (1997).
Buschmann, et al., "Spectroscopic Study and Evaluation of Red-Absorbing Fluorescent Dyes", Bioconjugate Chem. 14:195-204 (2003).
Canard, et al., "Catalytic Editing Properties of DNA Polymerases", Proc. Natl. Acad. Sci., 92:10859-10863 (1995).
Canard, et al., "DNA Polymerase Fluorescent Substrates with Reversible 3'-Tags", Gene, 148:1-6 (1994).
Crespo-Hernandez, et al., "Part 1. Photochemical and Photophysical Studies of Guanine Derivatives: Intermediates Contributing to its Photodestruction Mechanism in Aqueous Solution and the Participation of the Electron Adduct", Photochemistry and Photobiology, 71(5):534-543 (2000).
Greene, et al., "Protective Groups in Organic Synthesis", John Wiley & Sons, New York, pp. 67-74 & 574-576 (1999).
Greene, et al., "Protective Groups in Organic Synthesis", John Wiley & Sons, New York, pp. 17-21, 31-33, 35-39, 42-45, 114-115, 413, & 417 (1991).
Guibe, et al., "Allylic Protecting Groups and Their Use in a Complex Environment, Part I: Allylic Protection of Alcohols", Tetrahedron, 53(40):13509-13556 (1997).
Guibe, et al., "Allylic Protecting Groups and Their Use in a Complex Environment, Part II: Allylic Protecting Groups and Their Removal Through Catalytic Palladium pi-Allyl Methodology", Tetrahedron, 54(13):2967-3042 (1998).
Hayakawa, et al., "O-Allyl Protection of Guanine and Thymine Residues in Oligodeoxyribonucleotides", J. Organometallic Chemistry, 58:5551-5555 (1993).
Henner, et al., "Enzyme Action at 3' Termini of Ionizing Radiation-Induced DNA Strand Breaks", J. Biological Chemistry, 258:15198-15205 (1983).
Hovinen et al., "Synthesis of 3'-O-(ω-Aminoalkoxymethyl)thymidine 5-Triphosphates, Terminators of DNA Synthesis that Enable 3'-Labelling", JCS Perkin Trans I, 211-217 (1994).
Ikeda, et al., "A Non-Radioactive DNA Sequencing Method Using Biotinylated Dideoxynucleoside Triphospates and ΔTth DNA Polymerase", DNA Research, 2:225-227 (1995).
Jung et al., "Conversion of Alkyl Carbamates into Amines via Treatment with Trimethylsilyl Iodide," J.C.S. Chem. Comm., 7:315-316 (1978).
Kamal et al., "A Mild and Rapid Regeneration of Alcohols from Their Allylic Ethers by Chlorotrimethylsilane/Sodium Iodide", Tetrahedron Letters, 40:371-372 (1999).
Kitamura, et al., "(P(C6H5)3)CpRu+-Catalyzed Deprotection of Allyl Carboxylic Esters", J. Organic Chemistry, 67(14): 4975-4977 (2002).
Kloosterman, et al., "The Relative Stability of Allyl Ether, Allyloxycarbonyl Ester and Prop-2 Enylidene Acetal Protective Groups Toward Iridium, Rhodium and Palladium Catalysts", Tetrahedron Letters, 26(41):5045-5048 (1985).
Kocienski, "Protecting Groups", Georg Tieme Verlag, Stuttgart, 61-68 (1994).
Kraevskii, et al., "Substrate Inhibitors of DNA Biosynthesis", Translated from Molekulyarnaya Biologiya (Moscow) (Molecular Biology) 21(1):33-38 (1987).
Krecmerova, et al., "Synthesis of 5'-O-Phosphonomethyl Derivatives of Pyrimidine 2'-Deoxynucleosides", Collect. Czech. Chem. Commun. 55:2521-2536 (1990).
Kurata, et al., "Fluorescent Quenching-Based Quantitative Detection of Specific DNA/RNA Using a BODIPY® FL-Labeled Probe or Primer", Nucleic Acids Research, 29(6): E34 (2001).
Kvam, et al., "Characterization of Singlet Oxygen-Induced Guanine Residue Damage After Photochemical Treatment of Free Nucleosides and DNA", Biochimica et Biophysica Acta., 1217:9-15 (1994).
Li, et al., "A Photocleavable Fluorescent Nucleotide for DNA Sequencing and Analysis", Proc. Natl. Acad. Sci. 100:414-419 (2003).
Maier, et al., "Synthesis and Properties of New Fluorescein—Labeled Oligonucleotides", Nucleosides & Nucleotides, 14:961-965 (1995).
Markiewicz, et al., "A New Method of Synthesis of Fluorescently Labelled Oligonucleotides and Their Application in DNA Sequencing", Nucleic Acids Research, 25:3672-3680 (1997).
Marquez, et al., "Selective Fluorescence Quenching of 2,3-Diazabicyclo(2.2.2)oct-2-ene by Nucleotides", Organic Letters, 5:3911-3914 (2003).
Metzker, "Termination of DNA Synthesis by Novel 3'-Modified-Deoxyribonucleoside 5'-Triphosphases", Nucleic Acids Research, 22(20):4259-4267 (1994).
Nazarenko, et al., "Effect of Primary and Secondary Structure of Oligodeoxyribonucleotides on the Fluorescent Properties of Conjugated Dyes", Nucleic Acids Research, 30:2089-2095 (2002).
Nishino, et al., "Efficient Deanilidation of Phosphoranilidates by the Use of Nitrites and Acetic/Anhydride", Heteroatom Chemistry, 2:187-196 (1991).
Notice of Allowance mailed Jan. 17, 2013 in U.S. Appl. No. 13/432,989.
Notice of Allowance mailed Nov. 8, 2012 in U.S. Appl. No. 13/281,275.
Office Action mailed Mar. 1, 2013 in U.S. Appl. No. 13/316,204.
Oksman, et al., "Conformation of 3'-Substituted 2', 3'-Dideoxyribonucleosides in Aqueous Solution: Nucleoside Analogs with Potential Antiviral Activity", Nucleosides & Nucleotides, 10(1-3):567-568 (1991).
Oksman, et al., "Solution Conformations and Hydrolytic Stability of 2'- and 3'-Substituted 2', 3'-Dideoxyribonucleosides, Including Some Potential Inhibitors of Human Immunodeficiency Virus", Journal of Physical Organic Chemistry, 5(22):741-747 (1992).
Olejnik, et al., "Photocleavable Biotin Derivatives: A Versatile Approach for the Isolation of Biomolecules", Proc. Natl. Acad. Sci. 92:7590-7594 (1995).
Prober et al., "A System for Rapid DNA Sequencing with Fluorescent Chain-Terminating Dideoxynucleotides," Science, 238:336-341 (1987).
Quaedflieg, et al., "An Alternative Approach Towards the Synthesis of (3'→5') Methylene Acetal Linked Dinucleosides", Tetrahedron Letters, 33(21):3081-3084 (1992).
Rao, et al., "Four Color FRET Dye Nucleotide Terminators for DNA Sequencing", Nucleosides, Nucleotides, & Nucleic Acids, 20:673-676 (2001).
Rasolonjatovo, et al., "6-N-(N-Methylanthranylamido)-4-Oxo-Hexanoic Acid: A New Fluorescent Protecting Group Applicable to a New DNA Sequencing Method", Nucleosides & Nucleotides, 17:2021-2025 (1998).
Sarfati, et al., "Synthesis of Fluorescent Derivatives of 3'-O-(6-Aminohexanoyl)-pyrimidine Nucleosides 5'-Triphosphates that Act as DNA Polymerase Substrates Reversibly Tagged at C-3'", JCS Perkin Trans I, 1163-1171 (1995).
Seeger, "Single Molecule Fluorescence: High-Performance Molecular Diagnosis and Screening", Bioforum, Git Verlag, Darmstadt, DE, 21(4):179-185 (German text and English translation) (1998).
Torimura, et al., "Fluorescence-Quenching Phenomenon by Photoinduced Electron Transfer Between a Fluorescent Dye and Nucleotide Base", Analytical Sciences, 17:155-160 (2001).
Veeneman, et al., "An Efficient Approach to the Synthesis of Thymidine Derivatives Containing Phosphate-Isosteric Methylene Acetal Linkages", Tetrahedron, 47:1547-1562 (1991).
Wada, et al., "2-(Azidomethyl)benzoyl as a New Protecting Group in Nucleosides", Tetrahedron Letters, 42:1069-1072 (2001).
Welch, et al., "Syntheses of Nucleosides Designed for Combinatorial DNA Sequencing", Chemistry, European Journal, 5:951-960 (1999).

(56) References Cited

OTHER PUBLICATIONS

Yamashita, et al., "Studies of Antitumor Agents, VII. Antitumor Activities of O-Alkoxyalkyl Derivatives of 2'-Deoxy-5-trifluoromethyluridine", Chem. Pharm. Bull., 35:2373-2381 (1987).
Zavgorodny, et al., "1-Alkylthioalkylation of Nucleoside Hydroxyl Functions and its Synthetic Applications", Tetrahedron Letters, 32(51):7593-7596 (1991).
Zavgorodny, et al., "S,X-Acetals in Nucleoside Chemistry III. Synthesis of 2' and 3'-O-Azidomethyl Derivatives of Ribonucleosides", Nucleosides, Nucleotides & Nucleic Acids, 19(10-12):1977-1991 (2000).
Petition for Inter Partes Review of U.S. Pat. No. 7,057,026, dated Jan. 29, 2013.
Revised Petition for Inter Partes Review of U.S. Pat. No. 7,057,026, dated Feb. 7, 2013.
Petition for Inter Partes Review of U.S. Pat. No. 8,158,346, dated May 4, 2013.
Bystrom, et al., "ATP Analogs With Non-Transferable Groups in the Y Position as Inhibitors of Glycerol Kinase", Bioorganic & Medicinal Chemistry Letters, vol. 7, No. 20, 1997, 2613-2616.
Fuchs, "Handbook of Reagents for Organic Synthesis, Reagents for Silicon-Mediated Organic Synthesis", Purdue University, West Lafayette, IN, USA John Wiley & Sons Ltd, 2011, i-iv, 325-336.
Gitten, "Re-Examination U.S. Appl. No. 90/008,149, filed Aug 3, 2006, Re-Exam Certificate Issued on Dec 30, 2008", Aug. 3, 2006.
Gitten, "Re-Examination U.S. Appl. No. 90/008,152, filed Aug 3, 2006, Re-Exam Certificate Issued on Aug 12, 2008", Aug. 3, 2006.
Green, T.W. et al., "Protective Groups in organic synthesis", A Wiley-Interscience Publications, Jan. 1, 1999, 67-74, 474.
Greene, "Protective Groups in Organic Synthesis", John Wiley & Sons, Inc. 3rd ed. 1999, 1991, v-5, 17-33, 67-74, 96-99, 190-191, 260-261, 542-543, 701-719, 749-779.
Greene, et al., "Protective Groups in Organic Synthesis", John Wiley & Sons, New York, 1991, 42-45, and 417.
Greene, et al., "Protective Groups in Organic Synthesis", John Willey & Sons, New York, 1999, 1-316.
Greene, et al., "Protective Groups in Organic Synthesis", Third Edition, 1999, 17-245, 700-723.
Guiller, et al., "Linkers and cleavage Strategies in Solid-Phase Organic Synthesis and Combinatorial Chemistry", Chem. Rev. 100, 2000, 2091-2157.
Hayakawa, Y. et al., "A general approach to nucleoside 3'- and 5'-monophosphates", Tetrahedron Letters, vol. 28, 1987, 2259-2262.
IPR2013-00128, "Amended Complaint for Patent Infringement", dated Apr. 11, 2012.
IPR2013-00128, "Columbia University's Answer to Illumina's Amended Counterclaims for Declaratory Judgment", dated Jan. 7, 2013.
IPR2013-00128, "Columbia University's Response to Illumina's Requests for Admission", dated Apr. 8, 2013.
IPR2013-00128, "Curriculum Vitae Floyd Eric Romesberg", dated Aug. 2013.
IPR2013-00128, "Decision IBS's Motion for Pro Hac Vice Admission of Jason P. Grier", dated Jan. 10, 2014.
IPR2013-00128, "Decision Illumina's Motion for Pro Hac Vice Admission of William R. Zimmerman", dated Oct. 1, 2013.
IPR2013-00128, "Decision Institution of Inter Partes Review", dated Jul. 29, 2013.
IPR2013-00128, "Decision Motion to Withdraw", dated Sep. 10, 2013.
IPR2013-00128, "Decision", dated Apr. 26, 2013.
IPR2013-00128, "Declaration of Dr. Bruce Branchaud in Support of Petition for Inter Partes Review of U.S. Pat. No. 7,057,026", Jan. 28, 2013, 1-41.
IPR2013-00128, "Declaration of Dr. Bruce P. Branchaud in Support of Petition for Inter Partes Review of U.S. Pat. No. 7,057,026", dated Jun. 4, 2013.
IPR2013-00128, "Declaration of Eric Vermaas Accompanying Patent Owner's Motion to Amend", dated Oct. 24, 2013.
IPR2013-00128, "Declaration of Floyd Romesberg, Ph.D.", dated Oct. 24, 2013.
IPR2013-00128, "Declaration of Jason P. Grier in Support of Petitioner's Motion for Admission Pro Hac Vice of Jason P. Grier", dated Dec. 23, 2013.
IPR2013-00128, "Declaration of Ryan Drost", dated Sep. 12, 2012.
IPR2013-00128, "Declaration of William R. Zimmerman in Support of Motion to Appear Pro Hac Vice on Behalf of Patent Owner Illumina Cambridge Ltd.", dated Sep. 11, 2013.
IPR2013-00128, "Deposition Transcript of Bruce Branchaud, Ph.D. held on Oct. 3, 2013", dated Oct. 24, 2013.
IPR2013-00128, "English Translation of WO98/33939", dated Aug. 6, 1998.
IPR2013-00128, "ERRATA", dated Feb. 1, 2013.
IPR2013-00128, "Excerpts from the '026 file history", 2004-2005.
IPR2013-00128, "Exhibit List", dated Jan. 29, 2013.
IPR2013-00128, "Illumina Cambridge Limited Mandatory Notices", Feb. 18, 2013.
IPR2013-00128, "Illumina Cambridge Limited's Power of Attorney in an Inter Partes Review", dated Feb. 18, 2013.
IPR2013-00128, "Illumina Cambridge Limited's Updated Power of Attorney in an Inter Partes Review", dated Sep. 16, 2013.
IPR2013-00128, "Illumina Cambridge Ltd Preliminary Response", dated May 1, 2013.
IPR2013-00128, "Illumina Motion for Counsel to Withdraw From the Proceeding to Permit Substitution of Counsel", dated Aug. 30, 2013.
IPR2013-00128, "Illumina Motion to Seal", dated Oct. 24, 2013.
IPR2013-00128, "Illumina Notice of Cross-Examination Deposition of IBS Declarant Dr. Bruce P. Branchaud", dated Sep. 19, 2013.
IPR2013-00128, "Illumina Supplemental Mandatory Notice: Additional Backup Counsel", dated Oct. 1, 2013.
IPR2013-00128, "Illumina Updated Exhibit List", dated Oct. 24, 2013.
IPR2013-00128, "Illumina Updated Exhibit List", dated Sep. 23, 2013.
IPR2013-00128, "Illumina's Motion to Amend", dated Oct. 24, 2013.
IPR2013-00128, "Illumina's First Supplemental Mandatory Notices", dated Sep. 11, 2013.
IPR2013-00128, "Illumina's Second Supplemental Mandatory Notices", dated Sep. 17, 2013.
IPR2013-00128, "Intelligent Bio-System, Inc.'s Current Exhibit List", dated Dec. 23, 2013.
IPR2013-00128, "Intelligent Bio-System, Inc.'s Current Exhibit List", dated Sep. 17, 2013.
IPR2013-00128, "Intelligent Bio-Systems Inc.'s List of Proposed Motions", dated Aug. 27, 2013.
IPR2013-00128, "Intelligent Bio-Systems, Inc.'sS Responses to Illumina, Inc.'s First Set of Requests for Admission to IBS", dated Apr. 8, 2013.
IPR2013-00128, "Intelligent Bio-Systems' Notice of Cross-Examination Deposition of Illumina's Declarant Dr. Floyd Romesberg", dated Dec. 23, 2013.
IPR2013-00128, "Intelligent Bio-Systems' Notice of Cross-Examination Deposition of Illumina's Declarant Mr. Eric Vermaas", dated Dec. 23, 2013.
IPR2013-00128, "Intelligent Bio-Systems' Response to Order", dated Feb. 7, 2013.
IPR2013-00128, "List of Documents Considered by Floyd Romesberg, Ph.D., in Preparing Declaration", dated Oct. 24, 2013.
IPR2013-00128, "Motion for William R. Zimmerman to Appear Pro Hac Vice on Behalf of Patent Owner Illumina Cambridge Ltd.", dated Sep. 23, 2013.
IPR2013-00128, "Notice of Filing Date Accorded to Petition and Time for Filing Patent Owner Preliminary Response", dated Feb. 1, 2013.
IPR2013-00128, "Order (Regarding Conference Call)", dated Jan. 31, 2013.
IPR2013-00128, "Order Conduct of the Proceeding", dated Aug. 14, 2013.
IPR2013-00128, "Order Conduct of the Proceeding", dated Aug. 29, 2013.

(56) References Cited

OTHER PUBLICATIONS

IPR2013-00128, "Order Conduct of the Proceeding", dated Oct. 22, 2013.
IPR2013-00128, "Order Conduct of the Proceeding", dated Sep. 16, 2013.
IPR2013-00128, "Patent Owner Illumina's Additional Power of Attorney", dated Sep. 23, 2013.
IPR2013-00128, "Patent Owner Illumina's Proposed Motions", dated Aug. 27, 2013.
IPR2013-00128, "Petition for Inter Partes Review of U.S. Pat. No. 7,057,026", dated Jan. 29, 2013.
IPR2013-00128, "Petition for Inter Partes Review of U.S. Pat. No. 7,713,698", dated Sep. 16, 2012.
IPR2013-00128, "Petition for Inter Partes Review of U.S. Pat. No. 7,790,869", dated Sep. 16, 2012.
IPR2013-00128, "Petition for Inter Partes Review of U.S. Pat. No. 8,088,575", dated Oct. 3, 2012.
IPR2013-00128, "Petitioner's Motion for Admission Pro Hac Vice of Jason P. Grier", dated Dec. 23, 2013.
IPR2013-00128, "Petitioner's Motion for Admission Pro Hac Vice of Robert R. Baron, Jr.", dated Apr. 16, 2013.
IPR2013-00128, "Power of Attorney and Certificate of Service", dated Jan. 29, 2013.
IPR2013-00128, "Revised Petition for Inter Partes Review of U.S. Pat. No. 7,057,026", dated Feb. 7, 2013.
IPR2013-00128, "Scheduling Order", dated Jul. 29, 2013.
IPR2013-00128, "Signed Deposition Transcript of Dr. Bruce Branchaud", dated Oct. 3, 2013.
IPR2013-00128, "Transcript of Initial Conference Call Held on Aug. 29, 2013", dated Sep. 17, 2013.
IPR2013-00128, "U.S. Appl. No. 10/227,131", dated Aug. 23, 2002.
IPR2013-00128, "U.S. Pat. No. 7,057,026 File History", dated Oct. 24, 2013.
IPR2013-00266, "Curriculum Vitae Floyd Eric Romesberg", dated Dec. 30, 2013.
IPR2013-00266, "Decision IBS's Motion for Pro Hac Vice Admission of Jason P. Grier", dated Jan. 10, 2014.
IPR2013-00266, "Decision Illumina's Motion for Pro Hac Vice Admission of William R. Zimmerman", Dated Dec. 7, 2013.
IPR2013-00266, "Decision Institution of Inter Partes Review", dated Oct. 28, 2013.
IPR2013-00266, "Decision Intelligent Bio-Systems' Motion for Pro Hac Vice Admission of Robert R. Baron, Jr.", dated Aug. 9, 2013.
IPR2013-00266, "Decision Motion to Withdraw", dated Sep. 10, 2013.
IPR2013-00266, "Declaration of Dr. Bruce P. Branchaud in Support of Petition for Inter Partes Review of U.S. Pat. No. 8,158,346", dated May 3, 2013.
IPR2013-00266, "Declaration of Floyd Romesberg, Ph.D., in Support of Patent Owner's Motion to Amend", dated Dec. 30, 2013.
IPR2013-00266, "Declaration of Jason P. Grier in Support of Petitioner's Motion for Admission Pro Hac Vice of Jason P. Grier", dated Dec. 23, 2013.
IPR2013-00266, "Declaration of Robert R. Baron, Jr. in Support of Petitioner's Motion for Admission Pro Hac Vice of Robert R. Baron, Jr.", dated Jul. 19, 2013.
IPR2013-00266, "Declaration of William R. Zimmerman in Support of Motion to Appear Pro Hac Vice on Behalf of Patent Owner Illumina Cambridge Ltd.", dated Nov. 21, 2013.
IPR2013-00266, "Excerpts from the '346 Patent File History", dated May 4, 2013.
IPR2013-00266, "Excerpts from the file history of European Patent Application No. 02781434.2", dated May 4, 2013.
IPR2013-00266, "Exhibit List", dated May 4, 2013.
IPR2013-00266, "Illumina Cambridge Limited Mandatory Notices", dated May 24, 2013.
IPR2013-00266, "Illumina Cambridge Limited's Power of Attorney in an Inter Partes Review", dated May 24, 2013.
IPR2013-00266, "Illumina Cambridge Limited's Updated Power of Attorney in an Inter Partes Review", dated Sep. 16, 2013.
IPR2013-00266, "Illumina Cambridge Ltd Preliminary Response", dated Aug. 5, 2013.
IPR2013-00266, "Illumina Motion for Counsel to Withdraw From the Proceeding to Permit Substitution of Counsel", dated Aug. 30, 2013.
IPR2013-00266, "Illumina Motion to Seal", dated Dec. 30, 2013.
IPR2013-00266, "Illumina Updated Exhibit List", dated Dec. 30, 2013.
IPR2013-00266, "Illumina Updated Exhibit List", dated Nov. 21, 2013.
IPR2013-00266, "Illumina's Motion to Amend", dated Dec. 30, 2013.
IPR2013-00266, "Illumina's First Supplemental Mandatory Notices", dated Sep. 11, 2013.
IPR2013-00266, "Illumina's Second Supplemental Mandatory Notices", dated Sep. 17, 2013.
IPR2013-00266, "Intelligent Bio-System, Inc.'s Current Exhibit List", dated Dec. 23, 2013.
IPR2013-00266, "Intelligent Bio-Systems Inc.'s List of Proposed Motions", dated Nov. 14, 2013.
IPR2013-00266, "Inter Partes Review—Petitioner Power of Attorney", dated May 4, 2013.
IPR2013-00266, "List of Documents Considered by Floyd Romesberg, Ph.D., in Preparing Declaration", Dec. 30, 2013.
IPR2013-00266, "Motion for William R. Zimmerman to Appear Pro Hac Vice on Behalf of Patent Owner Illumina Cambridge Ltd", dated Nov. 21, 2013.
IPR2013-00266, "Notice of Filing Date Accorded to Petition and Time for Filing Patent Owner Preliminary Response", dated May 8, 2013.
IPR2013-00266, "Order Conduct of Proceeding", dated Aug. 29, 2013.
IPR2013-00266, "Order Conduct of the Proceeding", dated Nov. 26, 2013.
IPR2013-00266, "Patent Owner Illumina's Additional Power of Attorney", dated Nov. 21, 2013.
IPR2013-00266, "Patent Owner Illumina's Proposed Motions", dated Nov. 14, 2013.
IPR2013-00266, "Petition for Inter Partes Review of U.S. Pat. No. 7,713,698", dated Sep. 16, 2012.
IPR2013-00266, "Petition for Inter Partes Review of U.S. Pat. No. 7,790,869", dated Sep. 16, 2012.
IPR2013-00266, "Petition for Inter Partes Review of U.S. Pat. No. 8,088,575", dated Oct. 3, 2012.
IPR2013-00266, "Petition for Inter Partes Review of U.S. Pat. No. 8,158,346", dated May 4, 2013.
IPR2013-00266, "Petitioner's Motion for Admission Pro Hac Vice of Jason P. Grier", dated Dec. 23, 2013.
IPR2013-00266, "Petitioner's Motion for Admission Pro Hac Vice of Robert R. Baron, Jr", dated Jul. 19, 2013.
IPR2013-00266, "Redacted Declaration of Eric Vermaas Accompanying Patent Owner's Motion to Amend", dated Dec. 20, 2013.
IPR2013-00266, "Scheduling Order", dated Oct. 28, 2013.
IPR2013-00266, "*The Trustees of Columbia University in the City of New York v. Illumina, Inc.*", 1:12-cv-00376-GMS (D.Del.) Columbia's Answer to Illumina's Amended Counterclaims for Declaratory Judgment, Doc. 72, Jan. 7, 2013.
IPR2013-00266, "*The Trustees of Columbia University in the City of New York v. Illumina, Inc.*", 1:12-cv-00376-GMS (D.Del.), Columbia's Amended Complaint, Doc. 5, dated Apr. 11, 2012.
IPR2013-00324, "Decision Denying Institution of Inter Partes Review", dated Nov. 21, 2013.
IPR2013-00324, "Decision Intelligent Bio-Systems' Motion for Pro Hac Vice Admission of Robert R. Baron, Jr.", dated Aug. 9, 2013.
IPR2013-00324, "Decision Motion to Withdraw", dated Sep. 10, 2013.
IPR2013-00324, "Declaration of Dr. Bruce P. Branchaud in Support of Petition for Inter Partes Review of U.S. Pat. No. 7,057,026", dated Jun. 4, 2013.
IPR2013-00324, "Declaration of Robert R. Baron, Jr. in Support of Petitioner's Motion for Admission Pro Hac Vice of Robert R. Baron, Jr.", dated Jul. 19, 2013.

(56) References Cited

OTHER PUBLICATIONS

IPR2013-00324, "Excerpts from the '026 file history", dated Jun. 4, 2013.
IPR2013-00324, "Excerpts from the EP 02781434.2 File History", Oct. 13, 2008.
IPR2013-00324, "Exhibit List", dated Jun. 4, 2013.
IPR2013-00324, "Illumina Cambridge Limited Mandatory Notices", dated Jun. 24, 2013.
IPR2013-00324, "Illumina Cambridge Limited's Power of Attorney in an Inter Partes Review", dated Jun. 24, 2013.
IPR2013-00324, "Illumina Cambridge Limited's Updated Power of Attorney in an Inter Partes Review", dated Sep. 16, 2013.
IPR2013-00324, "Illumina Motion for Counsel to Withdraw From the Proceeding to Permit Substitution of Counsel", dated Aug. 30, 2013.
IPR2013-00324, "Illumina Notice of Waiver of Patent Owner Preliminary Response", dated Sep. 9, 2013.
IPR2013-00324, "Illumina's First Supplemental Mandatory Notices", dated Sep. 11, 2013.
IPR2013-00324, "Illumina's Second Supplemental Mandatory Notices", dated Sep. 17, 2013.
IPR2013-00324, "Intelligent Bio-System, Inc.'s Current Exhibit List", dated Jul. 19, 2013.
IPR2013-00324, "Inter Partes Review—Petitioner Power of Attorney", dated Jun. 4, 2013.
IPR2013-00324, "Notice of Filing Date Accorded to Petition and Time for Filing Patent Owner Preliminary Response", dated Jun. 4, 2013.
IPR2013-00324, "Notice of Filing Date Accorded to Petition and Time for Filing Patent Owner Preliminary Response", dated Jun. 6, 2013.
IPR2013-00324, "Order Conduct of the Proceeding", dated Aug. 29, 2013.
IPR2013-00324, "Petition for Inter Partes Review of U.S. Pat. No. 7,057,026", dated Jun. 4, 2013.
IPR2013-00324, "Petitioner's Motion for Admission Pro Hac Vice of Robert R. Baron, Jr.", dated Jul. 19, 2013.
IPR2013-00517, "Decision IBS's Motion for Pro Hac Vice Admission of Jason P. Grier", dated Dec. 23, 2013.
IPR2013-00517, "Decision IBS's Motion for Pro Hac Vice Admission of Jason P. Grier", dated Jan. 10, 2014.
IPR2013-00517, "Decision IBS's Motion for Pro Hac Vice Admission of Robert R. Baron, Jr.", dated Jan. 10, 2014.
IPR2013-00517, "Declaration of Dr. Bruce P. Branchaud in Support of Petition for Inter Partes Review of U.S. Pat. No. 7,566,537", dated Aug. 16, 2013.
IPR2013-00517, "Declaration of Jason P. Grier in Support of Petitioner's Motion for Admission Pro Hac Vice of Jason P. Grier", dated Dec. 23, 2013.
IPR2013-00517, "Declaration of Robert R. Baron, Jr. in Support of Petitioner's Motion for Admission Pro Hac Vice of Robert R. Baron, Jr.", dated Dec. 23, 2013.
IPR2013-00517, "Excerpts from the Deposition Transcript of Dr. Xiaohai Liu", dated Mar. 20, 2013.
IPR2013-00517, "Exhibit List", dated Aug. 19, 2013.
IPR2013-00517, "Illumina Notice of Waiver of Patent Owner Preliminary Response", dated Nov. 26, 2013.
IPR2013-00517, "Intelligent Bio-System, Inc.'s Current Exhibit List", dated Dec. 23, 2013.
IPR2013-00517, "Intelligent Bio-Systems, Inc.'s Response to Notice of Filing Date Accorded to Petition and Time for Filing Patent Owner Preliminary Response", dated Aug. 30, 2013.
IPR2013-00517, "Inter Partes Review—Petitioner Power of Attorney", dated Aug. 19, 2013.
IPR2013-00517, "Notice of Filing Date Accorded to Petition and Time for Filing Patent Owner Preliminary Response", dated Aug. 26, 2013.
IPR2013-00517, "Patent Owner Illumina's Power of Attorney", dated Sep. 9, 2013.
IPR2013-00517, "Patent Owner Submission of Mandatory Notice Information", dated Sep. 9, 2013.
IPR2013-00517, "Petition for Inter Partes Review of U.S. Pat. No. 7,566,537", dated Aug. 19, 2013.
IPR2013-00517, "Petition for Inter Partes Review of U.S. Pat. No. 7,713,698", dated Sep. 16, 2012.
IPR2013-00517, "Petition for Inter Partes Review of U.S. Pat. No. 7,790,869", dated Sep. 16, 2012.
IPR2013-00517, "Petition for Inter Partes Review of U.S. Pat. No. 8,088,575", dated Oct. 3, 2012.
IPR2013-00517, "Petitioner's Motion for Admission Pro Hac Vice of Jason P. Grier", dated Dec. 23, 2013.
IPR2013-00517, "Petitioner's Motion for Admission Pro Hac Vice of Robert R. Baron, Jr.", dated Dec. 23, 2013.
IPR2013-00517, "Revised Petition for Inter Partes Review of U.S. Pat. No. 7,566,537", dated Aug. 30, 2013.
IPR2013-00517, "Translation Affadavit for Loubinoux", Mar. 18, 2013.
IPR2013-00517, "U.S. Appl. No. 09/684,670", dated Oct. 6, 2000.
IPR2013-00518, "Decision IBS's Motion for Pro Hac Vice Admission of Jason P. Grier", dated Jan. 10, 2014.
IPR2013-00518, "Decision IBS's Motion for Pro Hac Vice Admission of Robert R. Baron, Jr.", dated Jan. 10, 2014.
IPR2013-00518, "Declaration of Dr. Bruce P. Branchaud in Support of Petition for Inter Partes Review of U.S. Pat. No. 7,566,537", dated Aug. 16, 2013.
IPR2013-00518, "Declaration of Jason P. Grier in Support of Petitioner's Motion for Admission Pro Hac Vice of Jason P. Grier", dated Dec. 23, 2013.
IPR2013-00518, "Declaration of Robert R. Baron, Jr. In Support of Petitioner'S Motion for Admission Pro Hac Vice of Robert R. Baron, Jr.", dated Dec. 23, 2013.
IPR2013-00518, "Excerpts from the '537 Patent File History", dated Aug. 19, 2013.
IPR2013-00518, "Excerpts from the file history of European Patent Application No. 02781434.2", dated Aug. 9, 2013.
IPR2013-00518, "Exhibit List", dated Aug. 19, 2013.
IPR2013-00518, "Illumina Notice of Waiver of Patent Owner Preliminary Response", dated Nov. 26, 2013.
IPR2013-00518, "Intelligent Bio-System, Inc.'s Current Exhibit List", dated Dec. 23, 2013.
IPR2013-00518, "Inter Partes Review—Petitioner Power of Attorney", dated Aug. 19, 2013.
IPR2013-00518, "Notice of Filing Date Accorded to Petition and Time for Filing Patent Owner Preliminary Response", dated Aug. 26, 2013.
IPR2013-00518, "Patent Owner Illumina's Power of Attorney", dated Sep. 9, 2013.
IPR2013-00518, "Patent Owner Submission of Mandatory Notice Information", dated Sep. 9, 2013.
IPR2013-00518, "Petition for Inter Partes Review of U.S. Pat. No. 7,566,537", dated Aug. 19, 2013.
IPR2013-00518, "Petition for Inter Partes Review of U.S. Pat. No. 7,713,698", dated Sep. 16, 2013.
IPR2013-00518, "Petition for Inter Partes Review of U.S. Pat. No. 7,790,869", dated Sep. 16, 2012.
IPR2013-00518, "Petition for Inter Partes Review of U.S. Pat. No. 8,088,575", dated Oct. 3, 2013.
IPR2013-00518, "Petitioner's Motion for Admission Pro Hac Vice of Jason P. Grier", dated Dec. 23, 2013.
IPR2013-00518, "Petitioner's Motion for Admission Pro Hac Vice of Robert R. Baron, Jr.", dated Dec. 23, 2013.
IPR2013-00518, "U.S. Appl. No. 09/684,670", dated Oct. 6, 2000.
Katagiri, et al., "Selective Protection of the Primary Hydroxyl Groups of Oxetanocn A and Conformational Analysis of O-Protected Oxetanocin A1", Chem. Pharm. Bull., vol. 43, No. 5,, 1995, 884-886.
Loubinoux, et al., "English Translation of Protection of Phenols by the Azidomethylene Group Application to the Synthesis of Unstable Phenols", Tetruhedron vol. 44, No. 19, 1988, 6055-6064.
Matsumoto, et al., "A Revised Structure of Pederin", 60 Tetrahedron Letters No. 60, 1968, 6297-6300.

(56) References Cited

OTHER PUBLICATIONS

Maxam, et al., "A new method for sequencing DNA", Proceedings of the National Academy of Sciences, vol. 74, No. 2, Feb. 1, 1977, 560-564.
Ruby, et al., "Affinity Chromatography with Biotynlated RNAs", Methods in Enxymology, vol. 181, 1990, 97-121.
Sanger, et al., "DNA sequencing with chain-terminating inhibitors", Proc. Natl. Acad. Sci. USA, vol. 74, No. 12, Biochemistry, Dec. 1977, 5463-5467.
Welch, et al., "Synthesis of Fluorescent, Photolabile 3'-O-Protected Nucleoside Triphosphates for the Base Addition Sequencing Scheme", Nucleosides & Nucleotides, 18(2), 1999, 197-201.
"Pierce Chemical Company", Products Catalog, 1999/2000.
Burns, et al., "Selective Reduction of Disulfides by Tris(2-carboxyethyl)phosphine", J. Org. Chem 56, 1991, 2648-2650.
Dawson, et al. "Affinity Isolation of Transcriptionally Active Murine Erythroleukemia Cell DNA Using a Cleavable Biotinylated Nucleotide Analog", The Journal of Biological Chemistry; vol. 264, No. 22, 1989, 12830-12837.
Handlon, et al., "Thiol Reduction of 3'-Azidothymidine to 3'-Aminothymidine: Kinetics and Biomedical Implications", Pharm. Res., 5, 1988, 297-99.
IPR2013-00128, " Proposed Protective Order in the *Trustees of Columbia University in the City of New York* v. *Illumina, Inc.*", Dec. 12, 2012.
IPR2013-00128, "Excerpts from the file history of European Patent Application No. 02781434.2", Aug. 16, 2006.
IPR2013-00128, "Illumina Notice of Cross-Examination Deposition of IBS Declarant Dr. Bruce P. Branchaud", Jan. 31, 2014.
IPR2013-00128, "Intelligent Bio-System, Inc.'s Current Exhibit List", Jan. 24, 2014.
IPR2013-00128, "Order Conduct of the Proceeding", Jan. 31, 2014.
IPR2013-00128, "Patent Owner's Unopposed Motion to File Substitute Declarations of Eric Vermaas and Floyd Romesberg, Ph.D., and to File Substitute Motion to Amend", Jan. 3, 2014.
IPR2013-00128, "Petitioner Intelligent Bio-Systems, Inc.'s Motion to Seal", Jan. 24, 2014.
IPR2013-00128, "Petitioner Intelligent Bio-Systems, Inc.'s Opposition to Illumina's Motion to Amend", Jan. 24, 2014.
IPR2013-00128, "Second Declaration of Dr. Bruce Branchaud in Support of Intelligent Bio-Systems, Inc.'s Opposition to Illumina's Motion to Amend", Jan. 24, 2014.
IPR2013-00128, "Substitute Declaration of Floyd Romesberg, Ph.D., in Support of Patent Owner'S Motion to Amend", Jan. 24, 2014.
IPR2013-00128, "Transcript of Video Deposition of Floyd Romesberg, Ph.D.", Jan. 24, 2014.
IPR2013-00128, "Trascript of Video Deposition of Eric Vermaas", Jan. 14, 2014.
Klausner, et al., "Dupont's DNA Sequencer Uses New Chemistry", Nature Publishing Group, Bio/technology; vol. 5, Nov. 1987, 1-2.
Letsinger, et al., "2,4-Dinitrobenzenesulfenyl as a Blocking Group for Hydroxyl Functions in Nucleosides", J. Org. Chem. 29, 1964, 2615-2618.
Lukesh, et al., "A Potent, Versatile Disulfide-Reducing Agent from Aspartic Acid", Jounal of the American Chemical Society; 134, 2012, 4057-4059.
Mitra, et al., "Fluorescent in situ sequencing on polymerase colonies", Analytical Biochemistry, Academic Press, San Diego US, vol. 320 No. 1, 2002, 55-65.
Murakami, et al., "Structure of a *Plasmodium yoelii* gene-encoded protein homoligiys to the Ca2+-ATPase of rabbit skeletal muscle sarcoplasmic reticulum", J. Cell Sci. 97, 1990, 487-95.
"Definitions of "viz"", The Oxford English Dictionary 1989; The Chambers Dictionary 1993; The Longman Dictionary of Contemporary English 2009.
"Getting published in Nature: the editorial process", Wayback Machine, 2008.
"Office Action mailed Dec. 14, 2012 in U.S. Appl. No. 13/437,772", Dec. 14, 2012.
"Office Action mailed Mar. 1, 2013 in U.S. Appl. No. 13/316,204", Mar. 1, 2013.
Bebenek, et al., "Frameshift errors initiated by nucleotide misincorporation", Proc. Natl. Acad. Sci. USA, vol. 87, Jul. 1990, 4946-4950.
IPR2013-00128, "Intelligent Bio-Systems' Notice of Cross-Examination Deposition of Illumina'SsDeclarant Dr. Floyd Romesberg", dated Dec. 23, 2013.
Bentley, et al., "Accurate whole human genome sequencing using reversible terminator chemistry", Nature, vol. 456, No. 7218, Nov. 6, 2008, 53-59.
Bi, et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis", J. Am. chem. Soc., 128, dated Oct. 20, 2005, 2542-2543.
Brown, et al., "Modern machine-aided methods of oligodeoxyribonucleotide synthesis", Oligonucleotides and Analogues, A Practical Approach, 1991, i-ii 1-11, 255.
Buschmann, et al., "Spectroscopic Study and Evaluation of Red-Absorbing Fluorescent Dyes", Bioconjugate Chem. 14: 195-204 (2003), 2003, 195-204.
C.A. No. 12-376 (GMS), "Videotaped Deposition of Dr Xiaohai Liu", dated Mar. 20, 2013.
Christensen, et al., "Specific Chemical Synthesis of Ribonucleoside 0-Benzyl Ethers", J. Org. Chem. vol. 37, No. 22, 1972, 3398-3401.
Dantas, et al., "Stannous chloride mediates single strand breaks in plasmid DNA through reactive oxygen species formation", Toxicology Letters 110, 1999, 129-136.
Dawson, et al., "Affinity Isolation of Active Murine Erythroleukemia Cell Chromatin: Uniform Distribution of Ubiquitinated Histone H2A Between Active and Inactive Fractions", Journal of Cellular Biochemistry 46, 1991, 166-173.
Definition of "VIZ", "Merriam-Webster's Collegiate Dictionary", 10th edition, 1997, 1316.
Fersht, et al., "DNA polymerase accuracy and spontaneous mutation rates: Frequencies of purinepurine, purinepyrimidine, and pyrimidine pyrimidine mismatches during DNA replication", Proc. Natl. Acad. Sci. USA, vol. 78, No. 7, Jul. 1981, 4251-4255.
Fersht, et al., "Fidelity of replication of phage OX174 DNA by DNA polymerase III holoenzyme: Spontaneous mutation by misincorporation", Proc. Natl. Acad. Sci. USA, vol. 76, No. 10, Oct. 1979, 4946-4950.
For Authors, "Getting published in Nature: the editorial process", nature.com, 2014.
Guo, "Molecular Engineering of Novel Nucleotide Analogues for DNA Sequencing and Analysis", Columbia University, 2009.
Guo, J. et al., "Four-color DNA sequencing with 3'-O-modified nucleotide reversible terminators and chemically cleavable fluorescent dideoxynucleotides", PNAS, 105(27), 2008, 9145-9150.
Holtzman, et al., "Electron microscopy of complexes of isolated acetylcholine receptor, biotinyl-toxin, and avidin", Proc. Natl. Acad. Sci. USA, vol. 79, Jan. 1982, 310-314.
IPR2013-00128, "Branchaud Second Depo Transcript", Dated Feb. 11, 2014.
IPR2013-00128, "Branchaud Signature page and Errata for Feb. 11, 2014 Deposition Transcript", dated Mar. 21, 2014.
IPR2013-00128, "Decision", dated Jul. 29, 2013.
IPR2013-00128, "Decision Patent Owner's Motion to File Substitute Declarations and Substitute Motion to Amend", dated Feb. 19, 2014.
IPR2013-00128, "Declaration of Adrienne Stephens", dated Mar. 17, 2014.
IPR2013-00128, "Deposition Transcript of Bruce Branchaud, Ph.D. held on Oct. 3, 2013", dated Oct. 8, 2013.
IPR2013-00128, "Excerpts from the file history of European Patent Application No. 02781434.2", Aug. 16, 2013.
IPR2013-00128, "File history excerpts from U.S. Appl. No. 10/285,010", dated Feb. 24, 2014.
IPR2013-00128, "Illumina Appendix of Authority for Its Opposition to IBS Motion to Exclude Evidence", dated Mar. 31, 2014.
IPR2013-00128, "Illumina Appendix of Authority for Its Reply to IBS Opposition to Illumina Motion to Exclude Evidence", dated Apr. 7, 2014.

(56) References Cited

OTHER PUBLICATIONS

IPR2013-00128, "Illumina Demonstratives for Oral Argument", dated Apr. 21, 2014.
IPR2013-00128, "Illumina Notice of Filing Its Demonstratives for Oral Hearing", dated Apr. 21, 2014.
IPR2013-00128, "Illumina Reply to IBS Opposition to Motion to Exclude", dated Apr. 7, 2014.
IPR2013-00128, "Illumina Updated Exhibit List", dated Apr. 21, 2014.
IPR2013-00128, "Illumina Updated Exhibit List", dated Feb. 19, 2014.
IPR2013-00128, "Illumina Updated Exhibit List", dated Feb. 24, 2014.
IPR2013-00128, "Illumina Updated Exhibit List", dated Mar. 18, 2014.
IPR2013-00128, "Illumina's Motion to Exclude IBS Evidence", dated Mar. 18, 2014.
IPR2013-00128, "Illumina's Request for Oral Argument", dated Mar. 18, 2014.
IPR2013-00128, "Illumina's Substitute Motion to Amend Under 37 C.F.R. § 42.121", dated Feb. 19, 2014.
IPR2013-00128, "Intelligent Bio-System, Inc.'s Current Exhibit List Under 37 C.F.R. § 42.63", dated Mar. 18, 2014.
IPR2013-00128, "Intelligent Bio-System, Inc.'s Current Exhibit List Under 37 C.F.R. § 42.63", dated Mar. 31, 2014.
IPR2013-00128, "Intelligent Bio-System, Inc.'s Current Exhibit List Under 37 C.F.R. § 42.63", dated Apr. 16, 2014.
IPR2013-00128, "Intelligent Bio-System's Objections to Illumina's Exhibits Submitted With Its Reply to Petitioner's Opposition to Illumina's Motion to Amend", dated Mar. 3, 2014.
IPR2013-00128, "Intelligent Bio-Systems, Inc.'s Opposition to Illumina's Motion to Exclude IBS Evidence", dated Mar. 31, 2014.
IPR2013-00128, "Intelligent Bio-Systems, Inc.'s Demonstratives for Apr. 23, 2014 Oral Argument", dated Apr. 16, 2014.
IPR2013-00128, "Inter Partes Review—Petitioner Power of Attorney", dated Apr. 15, 2014.
IPR2013-00128, "Order Conduct of the Proceeding", dated Apr. 11, 2014.
IPR2013-00128, "Order Trial Hearing", dated Mar. 31, 2014.
IPR2013-00128, "Patent Owner Illumina's Reply to Petitioner's Opposition to Illumina's Motion to Amend", dated Feb. 24, 2014.
IPR2013-00128, "Petitioner Intelligent Bio-Systems, Inc.'s Motion to Exclude Evidence", dated Mar. 18, 2014.
IPR2013-00128, "Petitioner Intelligent Bio-Systems, Inc.'s Reply to Illumina's Opposition to Intelligent Bio-Systems, Inc.'s Motion to Exclude Evidence", dated Apr. 7, 2014.
IPR2013-00128, "Petitioner Intelligent Bio-Systems, Inc.'s Request for Oral Argument", dated Mar. 18, 2014.
IPR2013-00128, "Petitioner Intelligent Bio-Systems, Inc.'s Supplemental Mandatory Notice: Additional Backup Counsel", dated Apr. 4, 2014.
IPR2013-00128, "Power of Attorney and Certificate of Service", dated Apr. 4, 2014.
IPR2013-00128, "Redlined Version—Illumina Motion to Amend", dated Feb. 19, 2014.
IPR2013-00128, "Redlined Version—Redacted Vermaas Declaration", dated Feb. 19, 2014.
IPR2013-00128, "Redlined Version—Romesberg Declaration", dated Feb. 19, 2014.
IPR2013-00128, "Romesberg signature page and errata for Jan. 14, 2014 depo transcriipt", dated Feb. 23, 2014.
IPR2013-00128, "ScanArray Express Brochure", 2002, 11 pages.
IPR2013-00128, "Substitute Declaration of Eric Vermaas Accompanying Patent Owner's Motion to Amend—Redacted", dated Jan. 24, 2014.
IPR2013-00128, "Substitute Declaratton of Erjc Vermaas Accompanying Patent Owner's Motion to Amend", dated Feb. 19, 2014.
IPR2013-00128, "Supplemental Information for Exhibit 1032", dated Jan. 27, 2014.

IPR2013-00128, "Vermaas signature page and errata for Jan. 13, 2014 depo transcript", dated Feb. 19, 2014.
IPR2013-00266, "Branchaud Deposition Transcript", dated Mar. 11, 2014.
IPR2013-00266, "Demonstrative Exhibits of Intelligent Bio-Systems, Inc. For Oral Hearing", dated May 28, 2014.
IPR2013-00266, "Errata Sheet for Bruce Branchaud, Ph.D. Deposition Taken: March 11, 2014", dated May 16, 2014.
IPR2013-00266, "Excerpts from Branchaud Deposition Transcript in related IPR2013-00128", dated Oct. 3, 2013.
IPR2013-00266, "Illumina Appendix of Authority", dated May 2, 2014.
IPR2013-00266, "Illumina Motion to Exclude IBS Evidence", dated Apr. 18, 2014.
IPR2013-00266, "Illumina Notice of Cross-Examination Deposition of IBS Declarant Dr. Bruce Branchaud", dated Mar. 4, 2013.
IPR2013-00266, "Illumina Objections to the Admissibility of IBS Evidence Served on February 28, 2014", dated Mar. 7, 2014.
IPR2013-00266, "Illumina Opposition to IBS Motion to Exclude Illumina Evidence", dated May 2, 2014.
IPR2013-00266, "Illumina Reply to IBS Opposition to Motion to Exclude", dated May 9, 2014.
IPR2013-00266, "Illumina Request for Oral Argument", dated Apr. 18, 2014.
IPR2013-00266, "Illumina Response to IBS Mot. for Observations on Romesberg Testimony", dated May 2, 2014.
IPR2013-00266, "Illumina Updated Exhibit List", dated Apr. 18, 2014.
IPR2013-00266, "Illumina Updated Exhibit List", dated Mar. 21, 2014.
IPR2013-00266, "Illumina's Notice of Filing Its Demonstratives (Exhibit 2060) for May 28, 2014 Oral Argument", dated May 22, 2014.
IPR2013-00266, "Illumina's Third Supplemental Mandatory Notice Re Backup Counsel—37 C.F.R. § 42.8 (a)(3)", dated May 21, 2014.
IPR2013-00266, "Illumina's Additional Power of Attorney", dated May 22, 2014.
IPR2013-00266, "Illumina's Demonstratives for Oral Agument", dated May 28, 2014.
IPR2013-00266, "Illumina's Updated Exhibit List", dated May 22, 2014.
IPR2013-00266, "Intelligent Bio-System, Inc.'s Current Exhibit List Under 37 C.F.R. § 42.63", dated May 2, 2014.
IPR2013-00266, "Intelligent Bio-System, Inc.'s Current Exhibit List Under 37 C.F.R. § 42.63", dated May 22, 2014.
IPR2013-00266, "Intelligent Bio-System, Inc.'s Current Exhibit List Under 37 C.F.R. § 42.63", dated Apr. 18, 2014.
IPR2013-00266, "Intelligent Bio-System, Inc.'s Current Exhibit List Under 37 C.F.R. § 42.63", dated Feb. 28, 2014.
IPR2013-00266, "Intelligent Bio-System, Inc.'s Current Exhibit List Under 37 C.F.R. § 42.63", dated May 16, 2014.
IPR2013-00266, "Intelligent Bio-System, Inc.'s Notice of Filing Its Demonstratives (EX. 1045) for May 28, 2014 Oral Argument", dated May 22, 2014.
IPR2013-00266, "Intelligent Bio-System's Objections to Illumina's Exhibits Submitted With Its Reply to Petitioner's Opposition to Illumina's Motion to Amend", dated Mar. 28, 2014.
IPR2013-00266, "Intelligent Bio-Systems, Inc.'s Opposition to Illumina's Motion to Exclude IBS Evidence", dated May 2, 2014.
IPR2013-00266, "Intelligent Bio-Systems' Notice of Cross-Examination Deposition of Illumina's Declarant Dr. Floyd Romesberg", dated Apr. 3, 2014.
IPR2013-00266, "Inter Partes Review—Petitioner Power of Attorney", dated Apr. 4, 2014.
IPR2013-00266, "Order Revised Scheduling Order 37 C.F.R. § 42.5", dated Apr. 4, 2014.
IPR2013-00266, "Order Trial Hearing", Apr. 29, 2014.
IPR2013-00266, "Patent Owner Illumina's Reply to Petitioner's Opposition to Illumina's Motion to Amend", dated Mar. 21, 2014.
IPR2013-00266, "Petitioner Intelligent Bio-Systems, Inc.'s Motion for Observations on the Cross-Examination Testimony of Floyd Romesberg, Ph.D.", dated Apr. 18, 2014.

(56) References Cited

OTHER PUBLICATIONS

IPR2013-00266, "Petitioner Intelligent Bio-Systems, Inc.'s Motion to Exclude Evidence", dated Apr. 18, 2014.
IPR2013-00266, "Petitioner Intelligent Bio-Systems, Inc.'s Motion to Seal Under 37 C.F.R. § 42.54", dated Feb. 28, 2014.
IPR2013-00266, "Petitioner Intelligent Bio-Systems, Inc.'s Opposition to Illumina's Motion to Amend", dated Feb. 28, 2014.
IPR2013-00266, "Petitioner Intelligent Bio-Systems, Inc.'s Request for Oral Argument", dated Apr. 18, 2014.
IPR2013-00266, "Petitioner Intelligent Bio-Systems, Inc.'s Supplemental Mandatory Notice: Additional Backup Counsel", dated Apr. 4, 2014.
IPR2013-00266, "Proposed Protective Order", dated Dec. 21, 2012.
IPR2013-00266, "Romesberg Errata and Signature Page", dated Apr. 10, 2014.
IPR2013-00266, "Second Declaration of Bruce Branchaud in related IPR2013-00128", dated Jan. 24, 2014.
IPR2013-00266, "Second Declaration of Dr. Bruce Branchaud in Support of Intelligent Bio-Systems, Inc.'s Opposition to Illumina's Motion to Amend", dated Feb. 28, 2014.
IPR2013-00266, "Second Declaration of Floyd Romesberg, Ph.D.", dated Mar. 21, 2014.
IPR2013-00266, "Second Declaration of Jason P. Grier", dated Mar. 21, 2014.
IPR2013-00266, "Video Deposition of Eric Vermaas in IPR2013-00128", dated Jan. 13, 2014.
IPR2013-00266, "Video Deposition of Floyd Romesberg, Ph.D.", dated Apr. 10, 2014.
IPR2013-00266, "Video Deposition of Floyd Romesberg, Ph.D. in IPR2013-00128", dated Jan. 14, 2014.
IPR2013-00517, "[Proposed] Protective Order", dated Dec. 21, 2012.
IPR2013-00517, "Automated forward and reverse ratcheting of DNA in a nanopore at 5-A precision", dated Jan. 7, 2013.
IPR2013-00517, "Curriculum Vitae Dr. Kevin Burgess", dated May 5, 2014.
IPR2013-00517, "Dae H. Kim Thesis Proposal Presentation", dated Jun. 28, 2007.
IPR2013-00517, "Decision—Institution of Inter Partes Review—37 CFR 42.108", dated Feb. 13, 2014.
IPR2013-00517, "Declaration of Floyd Romesberg, Ph.D.", dated May 5, 2014.
IPR2013-00517, "Declaration of Kevin Burgess, Ph.D.", dated May 5, 2014.
IPR2013-00517, "Declaration of Rosalyn M. Espejo Regarding Fed. R. Evid. 902(11) Certification of Records", dated May 5, 2014.
IPR2013-00517, "Declaration of William R. Zimmerman in Support of Motion to Appear Pro Hac Vice on Behalf of Patent Owner Illumina Cambridge Ltd.", dated Feb. 13, 2014.
IPR2013-00517, "Draft to Cao article", dated Sep. 18, 2008.
IPR2013-00517, "Email chain from Jerzy Olejnik to Andrew Gardner", dated Oct. 2, 2007.
IPR2013-00517, "Email Chain from Jerzy Olejnik to z179", dated Jun. 29, 2007.
IPR2013-00517, "Email chain from Jerzy Olenik to hc228 and Shiv Kumar", dated Feb. 1, 2008.
IPR2013-00517, "Email chain from Jerzy Olenik to msm2137", dated Jun. 3, 2007.
IPR2013-00517, "Email chain from Jim Russo to hc2278, Jia guo, Dae Kim, 1x2109, Zengmin Li, qm6, 1y2141, Jingyue Ju, Christine Rupp, Petra Lee Forde, Irina Morozova and John Edwards", dated Nov. 4, 2007.
IPR2013-00517, "Email chain from Steven Gordon to Jeffrey Arnold", dated Jun. 3, 2007.
IPR2013-00517, "Email chain from Steven Gordon to Jingyue Ju", dated Oct. 29, 2007.
IPR2013-00517, "Email from Bert Vogelstein to jre, Devin, jw2231, Jingyue Ju, Nickolas Papadopoulos and K8", dated Mar. 11, 2008.
IPR2013-00517, "Email from Bert Vogelstein to mysworld1982, dj222 and jrel3", dated Mar. 3, 2008.
IPR2013-00517, "Email from Huanyan Cao to Huanyan Cao, Jerzy Olejnik, Mong Sano Marma, Waldemar Szczepanik and Wojciech Czardybon", dated Mar. 4, 2009.
IPR2013-00517, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517, "Email from Jerzy Olejnik to Stephen Buchwald and Steven Gordon", dated Aug. 10, 2007.
IPR2013-00517, "Email from Jingyue Ju to Jingue Ju and Christine Rupp", dated Jun. 5, 2008.
IPR2013-00517, "Email from msm2137 to Jingyue Ju", dated Mar. 8, 2007.
IPR2013-00517, "Email from Shiv Kumar to Jerzy Olejnik and Jinguyue Ju", dated Jul. 5, 2012.
IPR2013-00517, "Facile Conversion of Adenosine Into New 2'-Substitlited-2'-Deoxy-Arabinofijrarosyladenine Derivatives: Stereospecific Syntheses of 2'-Azido-2'-Deoxy-,2'-Amino-Z'-Deoxy-, and Z'-Mercapto-Z'-Deoxy-O-D-Arabinofuranosilade", Tetrahedron Letters No. 45, 1978, 4341-4344.
IPR2013-00517, "Illumina Additional Power of Attorney", dated May 5, 2014.
IPR2013-00517, "Illumina Exhibit List", dated Mar. 13, 2014.
IPR2013-00517, "Illumina Motion to Seal Under 37 C.F.R. § 42.54", dated May 5, 2014.
IPR2013-00517, "Illumina Notice of Cross-Examination Deposition of IBS Declarant Dr. Bruce P. Branchaud", dated Mar. 25, 2014.
IPR2013-00517, "Illumina Updated Exhibit List", dated May 5, 2014.
IPR2013-00517, "Illumina Updated Mandatory Notice Regarding Designated Counsel", dated May 5, 2014.
IPR2013-00517, "Intelligent Bio-Systems Inc.'s List of Proposed Motions", dated Feb. 27, 2014.
IPR2013-00517, "Intelligent Bio-Systems, Inc., Cleavage", dated Aug. 2009.
IPR2013-00517, "Intelligent Bio-Systems, Inc., Custom Synthesis of Nucleotide Analogs", dated Aug. 1, 2012.
IPR2013-00517, "Intelligent Bio-Systems, Inc., Custom Synthesis of Nucleotide Analogs", dated May 6, 2008.
IPR2013-00517, "Intelligent Bio-Systems, Inc., Nucleotides", dated Jun. 15, 2011.
IPR2013-00517, "Inter Partes Review—Petitioner Power of Attorney", dated Apr. 4, 2014.
IPR2013-00517, "Invention Disclosure Form", dated Aug. 17, 2007.
IPR2013-00517, "Ju Lab Thesis Proposal", dated Mar. 19, 2007.
IPR2013-00517, "Ju Proposal", dated Nov. 29, 2006.
IPR2013-00517, "Ju Proposal", dated Nov. 6, 2007.
IPR2013-00517, "Lin Yu 3rd Year Research Presentation", dated May 2, 2008.
IPR2013-00517, "Motion for William R. Zimmerman to Appearpro Hac Vice on Behalf of Patent Owner Illumina Cambridge Ltd.", dated Mar. 13, 2014.
IPR2013-00517, "Note regarding Ju's Chemistry", dated May 5, 2014.
IPR2013-00517, "Notice of Allowance in U.S. Appl. No. 11/301,578", dated Apr. 30, 2009.
IPR2013-00517, "Notice of Stip to Change Due Dates 1 and 2", dated Apr. 7, 2014.
IPR2013-00517, "Order—Conduct of the Proceedings", dated Mar. 6, 2014.
IPR2013-00517, "Order Conduct of the Proceedings 37 .F.R. § 42.5", dated May 6, 2014.
IPR2013-00517, "Order Conduct of the Proceedings 37 .F.R. § 42.5", dated May 7, 2014.
IPR2013-00517, "Order—Patent Owner's Motion for William R Zimmerman to Appear Pro Hac Vice", dated Apr. 2, 2014.
IPR2013-00517, "Patent Owner Illumina's Proposed Motions", dated Feb. 27, 2014.
IPR2013-00517, "Petitioner Intelligent Bio-Systems, Inc.'s Supplemental Mandatory Notice: Additional Backup Counsel", dated Apr. 4, 2014.

(56) References Cited

OTHER PUBLICATIONS

IPR2013-00517, "Press Release—Illumina to acquire Solexa", dated 2006.
IPR2013-00517, "Qiagen's Dietrich Hauffe on Bringing Next-Generation Sequencing to clinical Research and Molecular Dx", Interview; http://www.genomeweb.com/print/1254496, dated Jul. 7, 2013.
IPR2013-00517, "Research Plan", dated Feb. 2, 2006.
IPR2013-00517, "Response to Office Action in U.S. Appl. No. 13/305,415", dated Aug. 14, 2013.
IPR2013-00517, "Scheduling Order", dated Feb. 13, 2014.
IPR2013-00517, "Transcript of Videotaped Deposition of •Bruce Branchaud, Ph.D. in IPR-2013-00128", dated Oct. 3, 2013.
IPR2013-00517, "Transcript of Videotaped Deposition of Bruce P. Branchaud in IPR-2013-000128", dated Feb. 11, 2014.
IPR2013-00517, "Transcript of Videotaped Deposition of Bruce P. Branchaud in IPR2013-00266", dated Mar. 11, 2014.
IPR2013-00517, "Videotaped Deposition of: Bruce P. Branchaud, Ph.D.", dated Apr. 8, 2014.
IPR2013-00517, "Yu, Sequencing by Synthesis with Cleavable Fluorescent Nucleotide Reversible Terminators (C-F-NRTs)", dated Oct. 20, 2008.
IPR2013-00518, "Decision—Institution of Inter Partes Review—37 CFR 42.108", dated Feb. 13, 2014.
IPR2013-00518, "Declaration of William R. Zimmerman in Support of Motion to Appear Pro Hac Vice on Behalf of Patent Owner Illumina Cambridge Ltd.", dated Mar. 11, 2014.
IPR2013-00518, "District Court Protective Order", dated Dec. 21, 2012.
IPR2013-00518, "Excerpts from File History EP App. No. 02781434.2", dated Jan. 24, 2014.
IPR2013-00518, "IBS's Opposition to Illumina's Motion to Amend", dated Jan. 24, 2014.
IPR2013-00518, "Illumina Exhibit List", dated Feb. 13, 2014.
IPR2013-00518, "Illumina Notice of Cross-Examination Deposition of IBS Declarant Dr. Bruce P. Branchaud", dated Mar. 25, 2014.
IPR2013-00518, "Illumina Request for Adverse Judgment Under 37 CFR § 42.73(b)(2)", dated May 5, 2014.
IPR2013-00518, "Intelligent Bio-Systems Inc.'s List of Proposed Motions", dated Feb. 27, 2014.
IPR2013-00518, "Inter Partes Review—Petitioner Power of Attorney", dated Apr. 4, 2014.
IPR2013-00518, "Judgment Request for Adverse Judgment 37 C.F.R. § 42.73(b)", dated May 6, 2014.
IPR2013-00518, "Motion for William R. Zimmerman to Appear Pro Hac Vice on Behalf of Patent Owner Illumina Cambridge Ltd.", dated Mar. 13, 2014.
IPR2013-00518, "Notice of Stipulation to Change Due Dates 1 and 2", dated Apr. 7, 2014.
IPR2013-00518, "Order—Conduct of the Proceeding 37 C.F.R. § 42.5", dated Jan. 31, 2014.
IPR2013-00518, "Order—Conduct of the Proceedings", dated Mar. 6, 2014.
IPR2013-00518, "Order—Patent Owner's Motion for William R. Zimmerman to Appear Pro Hac Vice", dated Apr. 2, 2014.
IPR2013-00518, "Patent Owner Illumina's Proposed Motions", dated Feb. 27, 2014.
IPR2013-00518, "Petitioner Intelligent Bio-Systems, Inc.'s Motion to Seal Under 37 C.F.R. § 42.54", dated Jan. 24, 2014.
IPR2013-00518, "Petitioner Intelligent Bio-Systems, Inc.'s Supplemental Mandatory Notice: Additional Backup Counsel", dated Apr. 4, 2014.
IPR2013-00518, "Scheduling Order", dated Feb. 13, 2014.
IPR2013-00518, "Substitute Declaration of Floyd Romesberg, Ph.D., In Support of Patent Owner's Motion to Amend", dated Jan. 24, 2014.
IPR2013-00518, "Video Deposition of Eric Vermaas January 13, 2014", dated Jan. 17, 2014.
IPR2013-00518, "Video Deposition of Floyd Romesberg, Ph.D.", dated Jan. 14, 2014.

Iye, et al., "Nucleoside Oxazaphospholidines as Novel Synthons in Oligonucleotide Synthesis", J. Org. Chem, 60, 1995, 5388-5389.
Ju, et al., "Four-color DNA sequencing by synthesis using cleavable fluorescent nucleotide reversible terminators", PNAS; vol. 103; No. 52, dated Dec. 26, 2006.
Ju, et al., "Four-color DNA sequencing by synthesis using cleavable fluorescent nucleotide reversible terminators", Columbia Genome Center, Columbia University College of Physicians and Surgeons; Department of chemical Engineering and Biomedical Engineering, Oct. 26, 2006, 19635-19640.
Kim, Dae H., "Four-Color DNA Sequencing by Synthesis on a Chip Using Cleavable Fluorescent Nucleotide Reversible Terminators", Columbia University, 2008.
Kit, Saul, "Deoxyribonucleic Acids", Division of Biochemical Virology, Baylor University College of Medicine, Houston Texas, Annu. Rev. Biochem, 1963, 43-82.
Lee, et al., "Unwinding of double-stranded DNA helix y dehydration", Proc. Natl. Acad. Sci. USA, vol. 78, No. 5, May 1981, 2838-2842.
Mardis, Elaine R., "A decade's perspective on DNA sequencing technology", Nature; vol. 470, Perspective; doi:10.1038/nature09796, Feb. 10, 2011, 198-203.
Meinwald, J., "An Approach to the Synthesis of Pederin", Pure and Appl. Chem., vol. 49, Pergoamon Press, 1977, 1275-1290.
Meng, et al., "Design and Synthesis of a Photocleavable Fluorescent Nucleotide 3'-O-Allyl-dGTP-PC-Bodipy-FL-510 as a Reversible Terminator for DNA Sequencing by Synthesis", JOC; 71, 2006, 3248-3252.
Meng, Qinglin, "PartI. Tandem Aldol-Allylation Reactions Promoted by Strained Silacycles", PartII. Design and Synthesis of Modified Fluorescent Nucleotides for DNA Sequencing by Synthesis, Columbiauniversity, 2006.
Mitra, et al., "Supplementary Information for Fluorescent in situ Sequencing on Polymerase Colonies", Analytical Biochemistry, 2003, 1-19.
Mullis, K.B. et al., "Specific Synthesis of DNA in Vitro via a Polymerase-Catalyzed Chain Reaction", Methods in Enzymology, vol. 155, Recmbinant DMA, part F, 1987, 19 pages.
Mungall, et al., "Use of the Azido Group in the Synthesis of 5' Terminal Aminodeoxythymidine Oligonucleotides", J. Org. Chem., vol. 40, No. 11, 1975.
O'Neil, et al., "The Merk Index", An Encyclopedia of Chemicals, Drugs, and Biologicals, Thirteenth Edition, 2001, 9815.
Pilard, et al., "A stereospecific synthesis of (±) α-conhydrine and (±) β-conhydrine.", Tetrahedron Letters, vol. 25, No. 15, 1984, 1555-1556.
Pugliese, et al., "Three-dimensional Structure of the Tetragonal Crystal Form of Egg-white Avidin in its Functional Complex with Biotin at 2 7 A Resolution", J. Mol. Biol., 1993, 698-710.
Qui, Chunmei, "Novel Molecular Engineering Approaches for Genotyping and DNA Sequencing", Columbia University, 2011.
Rigas, et al., "Rapid plasmid library screening using RecA-coated biotinylated probes", Proc. Natl. Acad. Sci. USA vol. 83, Genetics, Dec. 1986, 9591-9595.
Ruparel, et al., "Design and synthesis of a 3-O-allyl photocleavable fluorescent nucleotide as a reversible terminator for DNA sequencing by synthesis", PNAS, vol. 102, No. 17, dated Apr. 26, 2005, 5932-5937.
Shen, et al., "RNA structure at high resolution", The FASEB Journal, vol. 9, Aug. 1995, 1023-1033.
Shendure, et al., "Advanced sequencing technologies: methods and goals", Nature Rev. Genet., 5, 2004, 335-344.
Taylor, et al., "Rise per base pair in helices of double-stranded rotavirus RNA determined by electron microscopy", Virus Research, 2, 1985, 175-182.
Tietze, et al., "Synthesis of a Novel Stable GM.-Lactone Analogue as Hapten for a Possible Immunization Against Cancer", Angew. Chem. Int. Ed. Engl. 36, No. 15, 1997, 1615-1617.
Watkins, et al., "Synthesis of Oligodeoxyribonucleotides Using N-Benzyloxycarbonyl-Blocked Nucleosides", J. Am. Chem. Soc. 104, 1982, 5702-5708.
Watson, et al., "Molecular Biology of the Gene; 5th edition", The Structures of DNA and RNA; Chapter 6, 2004, 97-128.

(56) References Cited

OTHER PUBLICATIONS

Westheimer, F.H., "Why Nature Chose Phosphates", Science, vol. 235, www.sciencemag.org, Mar. 6, 1987, 1174-1178.
Wu, et al., "3-O-modified nucleotides as reversible terminators for pyrosequencing", PNAS; vol. 104; No. 42, Oct. 16, 2007, 16462-16467.
Wu, et al., "Termination of DNA synthesis by N6-alkylated, not 3'-O-alkylated, photocleavable 2'-deoxyadenosine triphosphates", Nucleic Acids Research, vol. 35, No. 19, 2007, 6339-6349.
Wu, Jian, "Molecular Engineering of Novel Nucleotide Analogues for DNA Sequencing by Synthesis", Columbia University, 2008.
Yoshimoto, et al., "Tris(2,4,6-trimethoxyphenyl)phosphine (TTMPP): A Novel Catalyst for Selective Deacetylation", Chemistry Letters, Department of Chemistry, Faculty of Science, Kobe University, Kobe 657-8501, 2001, 934-935.
Zavgorodny, et al., "1-Alkylthioalkylation of Nucleoside Hydroxyl Functions and its synthetic applications", Tetrahedron Letters vol. 32 No. 51, 1991, 7593-7596.
Zimmerman, Eilene, "The Smartest Company in the World. And It's Not Google", MIT Tech Review vol. 117, No. 2, dated Mar./Apr. 2014, 27-29.
IPR2013-00128 # 1, "Proceedings", Apr. 23, 2014.
IPR2013-00128 # 2, "Decision, Motion to Seal", Jun. 4, 2014.
IPR2013-00128 # 3, "Petitioner Intelligent Bio-Systems, Inc.'s Updated Mandatory Notice of Counsel", Jun. 6, 2014.
IPR2013-00128 # 4, "Final Written Decision", Jul. 25, 2014.
IPR2013-00128 # 5, "Decision, Request to Preserve Recording Pending Appeal", Sep. 10, 2014.
IPR2013-00128 # 6, "Renewed Motion for Attorneys to Withdraw as Backup Counsel for Illumina", Sep. 23, 2014.
IPR2013-00128 # 7, "Illumina Notice of Appeal in the U.S. Court of Appeals for the Federal Circuit", Sep. 24, 2014.
IPR2013-00128 # 8, "Decision, Motion to Withdraw", Oct. 7, 2014.
IPR2013-00128 # 9, "Petitioner Intelligent Bio-Systems, Inc.'s Supplemental Mandatory Notice: Additional Backup Counsel", Jun. 3, 2014.
IPR2013-00128 # 10, "Illumina Revocation of Power of Attorney for James G. Morrow and James D. Borchardt", Oct. 27, 2014.
IPR2013-00266 # 1, "Petitioner Intelligent Bio-Systems, Inc.'s Updated Mandatory Notice of Counsel", Jun. 6, 2014.
IPR2013-00266 # 2, "Decision, Motion to Seal", Jun. 16, 2014.
IPR2013-00266 # 3, "Proceedings", Jul. 8, 2014.
IPR2013-00266 # 4, "Renewed Motion for Attorneys to Withdraw as Backup Counsel for Illumina", Jul. 29, 2014.
IPR2013-00266 # 5, "Decision, Motion to Withdraw", Oct. 7, 2014.
IPR2013-00266 # 6, "Illumina Revocation of Power of Attorney for James G. Morrow and James D. Borchardt", Oct. 27, 2014.
IPR2013-00266 # 7, "Final Written Decision", Oct. 28, 2014.
IPR2013-00266 # 8, "Erratum", Oct. 28, 2014.
IPR2013-00324 # 1, "Intelligent Bio-Systems, Inc. Request for Refund of Post-Institution Fee", Mar. 3, 2014.
IPR2013-00324 # 2, "Notice of Refund", Mar. 4, 2014.
IPR2013-00517 # 1, "Petitioner Intelligent Bio-Systems, Inc.'s Supplemental Mandatory Notice: Additional Backup Counsel", Jun. 3, 2014.
IPR2013-00517 # 2, "Power of Attorney", Jun. 3, 2014.
IPR2013-00517 # 3, "Petitioner Intelligent Bio-Systems, Inc.'s Corrected Supplemental Mandatory Notice: Additional Backup Counsel", Jun. 3, 2014.
IPR2013-00517 # 4, "Petitioner Intelligent Bio-Systems, Inc.'s Response to Illumina's Motion to Seal", Jun. 5, 2014.
IPR2013-00517 # 5, "Petitioner Intelligent Bio-Systems, Inc.'s Updated Mandatory Notice of Counsel", Jun. 3, 2014.
IPR2013-00517 # 6, "Notice of Stipulation to Change Due Date 2", Jun. 23, 2014.
IPR2013-00517 # 7, "Intelligent Bio-System's Notice of Cross-Examination Deposition of Illumina's Declarant Dr. Floyd Romesberg", Jun. 26, 2014.
IPR2013-00517 # 8, "Intelligent Bio-Systems' Notice of Cross-Examination Deposition of Illumina's Declarant Dr. Kevin Burgess", Jun. 27, 2014.
IPR2013-00517 # 9, "Declaration of Derek C. Walter in Support of Motion to Appear Pro Hac Vice on Behalf of Patent Owner Illumina Cambridge Ltd.", Jun. 23, 2014.
IPR2013-00517 # 10, "Illumina Updated Exhibit List", Jul. 7, 2014.
IPR2013-00517 # 11, "Motion for Derek C. Walter to Appear Pro Hac Vice on Behalf of Patent Owner Illumina Cambridge Ltd.", Jul. 7, 2014.
IPR2013-00517 # 12, "Illumina Reply to IBS Opposition to Illumina Motion to File Under Seal", Jul. 7, 2014.
IPR2013-00517 # 13, "Illumina Updated Mandatory Notice Adding Sheila N. Swaroop as Additional Backup Counsel", Jul. 7, 2014.
IPR2013-00517 # 14, "Illumina Additional Power of Attorney", Jul. 11, 2014.
IPR2013-00517 # 15, "Decision Illumina's Motion for Pro Hac Vice Admission of Derek C. Walter", Jul. 15, 2014.
IPR2013-00517 # 16, "Illumina Updated Mandatory Notice Adding Derek C. Walter as Additional Backup Counsel", Jul. 18, 2014.
IPR2013-00517 # 17, "Liu Transcript p. 295, Exhibit 1022", Jul. 28, 2014.
IPR2013-00517 # 18, "Biophysical Society, Abstracts, Sixth Annual Meeting", Feb. 14-16, 1962.
IPR2013-00517 # 19, Ireland, et al., "Approach to the Total Synthesis of Chlorothricolide: Synthesis of (+)-19,20-Dihydro-24-O-metylchlorothricolide. Methyl Ester, Ethyl Carbonate", J. Org. Chem. 51, 1986, Jul. 28, 2014, 685-648.
IPR2013-00517 # 20, Kamal et al., "A Mild and Rapid Regeneration of Alcohols from their Allylic Ethers by Chlorotrimethylsilane/Sodium Iodide", Tetrahedrom Letters 40, 1999, Jul. 28, 2014, 31-372.
IPR2013-00517 # 21, "Videotaped Deposition of Kevin Burgess, Ph.D., taken before Greg S. Weiland, CSr, RMR, CRR, pursuant to the Applicable Rules Pertaining to the Taking of Depositions", Jul. 28, 2014.
IPR2013-00517 # 22, "Video Deposition of Floyd Romesberg, Ph.D.", Jul. 8, 2014.
IPR2013-00517 # 23, "Prosecution History Excerpt, Restriction Requirement", Jul. 12, 2007.
IPR2013-00517 # 24, "The American Heritage College Dictionary, Third Edition", Jul. 28, 2014.
IPR2013-00517 # 25, Faucher et al., "Tris(2-Carboxyethyl)phosphine (TCEP) for the Reduction of Sulfoxides, Sulfonylchlorides, N-Oxides, and Azides", Synthetic Communications vol. 33, No. 22, 2003, 3503-3511.
IPR2013-00517 # 26, Variagenics, Inc., "WO 02/210098", Mar. 14, 2002.
IPR2013-00517 # 27, Saxon et al., "Cell Surface Engineering by a Modified Staudinger Reaction", Science vol. 287, Mar. 17, 2000.
IPR2013-00517 # 28, Furniss et al., "Vogel's Textbook of Practical Organic Chemistry, Fifth Edition", 1989.
IPR2013-00517 # 29, Gololobov et al., "Recent Advances in the Staudinger Reaction", Tetrahedron, vol. 48, No. 8, 1992, 1353-1406.
IPR2013-00517 # 30, "Second Declaration of Dr. Bruce Branchaud in Support of Intelligent Bio-Systems, Inc.'s Reply to Illumina's Patent Owner Response", Jul. 28, 2014.
IPR2013-00517 # 31, Hyman, "U.S. Pat. No. 5,602,000", Feb. 11, 1997.
IPR2013-00517 # 32, Chen, "DNA polymerases drive DNA sequencing-by-synthesis technologies: both past and present", Frontiers in Microbiology, Review Article,, Jun. 24, 2014.
IPR2013-00517 # 33, Chang et al., "Molecular Biology of Terminal Transferase", CRC Critical Reviews in Biochemistry, vol. 21, Issue 1, Jul. 28, 2014, 27- 52.
IPR2013-00517 # 34, Mag et al., "Synthesis and selective cleavage of oligodeoxyribonucleotides containing non-chiral internucleotide phosphoramidate linkages", Nucleic Acids Research, vol. 17, No. 15, 1989.
IPR2013-00517 # 35, Laidler et al., "Chemical Kinetics, Third Edition", 1987, 10-11.
IPR2013-00517 # 36, "Park IP Translations", Jun. 30, 2014.

(56) References Cited

OTHER PUBLICATIONS

IPR2013-00517 # 37, Knouzi et al., "English Translation", Aug. 2, 1985.
IPR2013-00517 # 38, Knouzi et al., "Reduction d'azides par la triphenylphosphine en presence d'eau: une methode generale et chimioselective d'acces auz amines primaires", Feb. 8, 1985, 815-819.
IPR2013-00517 # 39, Smith et al., "US Patent Application Publication No. 2006/0240439", Oct. 26, 2006.
IPR2013 -00517 # 40, Bentley, "Supplemental Information", Nature, doi: 10.1038/nature07517, Jul. 28, 2014.
IPR2013-00517 # 41, Kirby, "A New Method for the Isolation of Deoxyribonucleic Acids: Evidence on the Nature of Bonds between Deoxyribonucleic Acid and Protein", Renal Clearance of 17-oxo Steroid Conjugates, vol. 66, 1957, 495-504.
IPR2013-00517 # 42, Efimov et al., "An Azidomethyl Protective Group in the Synthesis of Oligoribonucleotides by the Phosphotriester Method", Letters to the Editor, Russian Journal of Bioorganic Chemistry, vol. 35, No. 2, 2009, 250-253.
IPR2013-00517 # 43, Levine et al., "The Relationship of Structure to the Effectiveness of Denaturing Agents for Deoxyribonucleic Acid", Biochemistry, vol. 2, No. 1, Jan.-Feb. 1963, 168-175.
IPR2013-00517 # 44, Leberton et al., "Structure-Immunosuppressive Activity Relationships of New Analogues of 15-Deoxyspergualin. 2. Structural Modifications of the Spermidine Moiety", J. Med. Chem. 42, 1999, 4749-4763.
IPR2013-00517 # 45, "Declaration of Dr. Michael Metzker in Support of Intelligent Bio-Systems, Inc.'s Reply to Illumina's Patent Owner Response", Jul. 28, 2014.
IPR2013-00517 # 46, "Petitioner Intelligent Bio-Systems, Inc.'s Motion to Seal Under 37 C.F.R. 42.54", Jul. 28, 2014.
IPR2013-00517 # 47, "Intelligent Bio-System, Inc.'s Current Exhibit List Under 37 C.F.R., 42.63", Jul. 28, 2014.
IPR2013-00517 # 48, "Petitioner Intelligent Bio-Systems' Reply to Illumina's Patent Owner Response", Jul. 28, 2014.
IPR2013-00517 # 49, "Order Conduct of the Proceeding", Jul. 29, 2014.
IPR2013-00517 # 50, "Illumina Notice of Cross-Examination Deposition of IBS Declarant Dr. Michael L. Metzker", Aug. 1, 2014.
IPR2013-00517 # 51, "Illumina Notice of Cross-Examination Deposition of IBS Declarant Dr. Bruce P. Branchaud", Aug. 12, 2014.
IPR2013-00517 # 52, "Patent Owner's email for request for Authorization to File *IBS* v *Illumina*", Aug. 20, 2014.
IPR2013-00517 # 53, "Intelligent Bio-System's Objections to Illumina's Exhibits Marked at Dr. Branchaud's Deposition", Sep. 2, 2014.
IPR2013-00517 # 54, "Intelligent Bio-System's Objections to Illumina's Exhibits Marked at Dr. Metzker's Deposition", Aug. 19, 2014.
IPR2013-00517 # 55, "Intelligent Bio-System's Objections to Illumina's Exhibits Submitted with its Patent Owner Response", May 19, 2014.
IPR2013-00517 # 56, "Intelligent Bio-System, Inc.'s Current Exhibit List Under 37 C.F.R., 42.63", Sep. 2, 2014.
IPR2013-00517 # 57, "Petitioner Intelligent Bio-Systems, Inc.'s Request for Oral Argument", Sep. 2, 2014.
IPR2013-00517 # 58, "Petitioner Intelligent Bio-Systems, Inc.'s Motion to Exclude Evidence", Sep. 2, 2014.
IPR2013-00517 # 59, "Illumina's Motion for Observations on the Cross-Examination Testimony of Bruce Branchaud, Ph.D. And Michael Metzker, Ph.D.", Sep. 2, 2014.
IPR2013-00517 # 60, "Illumina Motion to Seal Under 37 C.F.R. 42.54", Sep. 2, 2014.
IPR2013-00517 # 61, "Illumina's Motion to Exclude evidence Pursuant to 37 C.R.F., 42.64(c)", Sep. 2, 2014.
IPR2013-00517 # 62, "Illumina Request for Oral Argument", Sep. 2, 2014.
IPR2013-00517 # 63, "Illumina Updated Exhibit List", Sep. 2, 2014.
IPR2013-00517 # 64, "Videotaped sworn testimony of Bruce P. Branchaud, Ph.D.", Sep. 2, 2014.
IPR2013-00517 # 65, "Videotaped Deposition of Michael L. Metzker, Ph.D.", Aug. 12, 2014.
IPR2013-00517 # 66, "Illumina Objections to Admissibility of IBS Evidence Served With Reply", Aug. 4, 2014.
IPR2013-00517 # 67, Reardon et al., "Reduction of 3'-Azido-3"-deoxythymidine (AZT) and AZT Nucleotides by Thiols", The Journal of Biological Chemistry, vol. 269, No. 23, Jun. 10, 1994, 15999-16008.
IPR2013-00517 # 68, Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives", Tetrahedron 56, 2000, 6269-6277.
IPR2013-00517 # 69, Aldrich, "Fine Chemicals", Aldrich Chemical Company, Inc, 1986.
IPR2013-00517 # 70, Wu et al., "Termination of DNA synthesis by N6- alkylated, not 3'O-alkylated, photocleavable 2'-deoxyadenosine triphosphates", Nucleic Acids Research, vol. 35, No. 19, 2007, 6339-6349.
IPR2013-00517 # 71, "Initial sequencing and analysis of the human genome", Nature, vol. 409, 2001, 850-921.
IPR2013-00517 # 72, Gardner et al., "Rapid incorporation kinetics and improved fidelity of a novel class of 3'-OH unblocked reversible terminators", Nucleic Acids Research, vol. 40, No. 15, May 8, 2012, 7404-7415.
IPR2013-00517 # 73, Mussini et al., "Criteria for Standardization of pH Measurements in Organic Solvents and Water + Organic Solvent Mixtures of Moderate to High Permittivities", Pure & Appl. Chem., vol. 57, No. 6, 1985, 865-876.
IPR2013-00517 # 74, O'Neil, et al., "The Merck Index, an Encyclopedia of Chemicals, Drugs, and Biologicals, Thirteenth Edition", 2001.
IPR2013-00517 # 75, Metzker, "US Publication No. 2003/0180769", Sep. 25, 2003.
IPR2013-00517 # 76, Hanlon, "The importance of London dispersion forces in the maintenance of the deoxyribonuleic acid helix", Biochemical and Biophysical Research Communications, vol. 23, No. 6, 1966.
IPR2013-00517 # 77, Treinin, "General and theoretical aspects, Chapter I, The Chemistry of the Azido Group, Edited by Saul Patai", 1971.
IPR2013-00517 # 78, Tsai et al., "Versatile and Efficient Synthesis of a New Class of Aza-Based Phosphinic Amide Ligands via Unusual P-C Cleavage", Helvetica Chimica Acta, vol. 89, 2006, 3007-3017.
IPR2013-00517 # 79, Metzker, "Sequencing technologies—the next generation", Nature Reviews, Genetics, vol. 11, Jan. 2010, 31-46.
IPR2013-00517 # 80, "Intelligent Bio-Systems, Inc.'s Opposition to Illumina's Motion to Exclude Evidence", Sep. 15, 2014.
IPR2013-00517 # 81, "IBS's response to Illumina's motion for observations on the cross-examination testimony of Bruce Branchaud, Ph.D., and Michael Metzker, Ph.D.", Sep. 15, 2014.
IPR2013-00517 # 82, "Answer and Counterclaims of Defendant Intelligent Bio-Systems, Inc.", Sep. 18, 2013.
IPR2013-00517 # 83, "Declaration of Rosalyn M. Espejo Regarding Fed.R. Evid. 902(11) Certification of Records", Jun. 2, 2014.
IPR2013-00517 # 84, "Illumina Updated Exhibit List", Sep. 15, 2014.
IPR2013-00517 # 85, "Illumina's Opposition to IBS Motion to Exclude Evidence", Sep. 15, 2014.
IPR2013-00517 # 86, "Illumina Motion to Seal Under 37 C.F.R. 42.54", Sep. 15, 2014.
IPR2013-00517 # 86, "Order, Trial Hearing", Sep. 17, 2014.
IPR2013-00517 # 88, "Illumina's Reply to IBS's Opposition to Illumina's Motion to Exclude", Sep. 22, 2014.
IPR2013-00517 # 89, "Emails re IBS withdrawing its hearsay objections", Jul. 31, 2014.
IPR2013-00517 # 90, "Errata Sheet for Bruce Branchaud, Ph.D. Deposition", Taken: Aug. 26, 2014.
IPR2013-00517 # 91, "Errata Sheet for Michael L. Metzker, Ph.D. Deposition", Taken: Aug. 12, 2014.

(56) References Cited

OTHER PUBLICATIONS

IPR2013-00517 # 92, "Petitioner Intelligent Bio-Systems, Inc.'s Reply to Illumina's Opposition to Intelligent Bio-Systems, Inc.'s Motion to Exclude Evidence", Sep. 22, 2014.
IPR2013-00517 # 93, "Intelligent Bio-System, Inc.'s Current Exhibit List Under 37 C.F.R. 42.63", Sep. 22, 2014.
IPR2013-00517 # 94, Judge Lora M. Green et al., "Illumina's Demonstratives for Oral Hearing", Oct. 10, 2014.
IPR2013-00517 # 95, "Illumina Updated Exhibit List", Oct. 3, 2014.
IPR2013-00517 # 96, "Illumina Notice of Filing and Serving Its Demonstratives (Ex. 2156) for Oral Argument", Oct. 3, 2014.
IPR2013-00517 # 97, "Illumina Additional Power of Attorney for Jeff Costakos", Oct. 3, 2014.
IPR2013-00517 # 98, "Illumina Updated mandatory Notice Adding Jeffrey N. Costakos as Additional Backup Counsel", Oct. 3, 2014.
IPR2013-00517 # 99, Judge Lora M. Green et al., "Demonstrative Exhibits of Intelligent Bio-Systems, Inc. For Oral Hearing", Oct. 10, 2014.
IPR2013-00517 # 100, "Intelligent Bio-System, Inc.'s Notice of Filing Its Demonstratives (Ex. 1062) for Oct. 10, 2014 Oral Argument", Oct. 3, 2014.
IPR2013-00517 # 101, "Intelligent Bio-System, Inc.'s Current Exhibit List Under 37 C.F.R. 42.63", Oct. 3, 2014.
IPR2013-00517 # 102, Intelligent Bio-Systems, Inc.'s Answer, Affirmative Defenses & Counterclaims to Illumina, Inc. and Illumina Cambridge Ltd.'s Second Amended Counterclaims to Amended Complaint, dated Jan. 7, 2013.
IPR2013-00517 # 103, "Dae H. Kim Thesis Proposal Presentation", dated Jun. 28, 2007.
IPR2013-00517 # 104, "Draft to Cao article", dated Sep. 18, 2008.
IPR2013-00517 # 105, "Email chain from Jerzy Olejnik to Andrew Gardner", dated Oct. 2, 2007.
IPR2013-00517 # 106, "Email Chain from Jerzy Olejnik to z179", dated Jun. 29, 2007.
IPR2013-00517 # 107, "Email chain from Jerzy Olenik to hc228 and Shiv Kumar", dated Feb. 1, 2008.
IPR2013-00517 # 108, "Email chain from Jerzy Olenik to msm2137", dated Jun. 3, 2007.
IPR2013-00517 # 109, "Email chain from Jim Russo to hc2278, Jia guo, Dae Kim, 1x2109, Zengmin Li, qm6, 1y2141, Jingyue Ju, Christine Rupp, Petra Lee Forde, Irina Morozova and John Edwards", dated Nov. 4, 2007.
IPR2013-00517 # 109, "Email chain from Steven Gordon to Jingyue Ju", dated Oct. 29, 2007.
IPR2013-00517 # 110, "Email chain from Steven Gordon to Jeffrey Arnold", dated Jun. 3, 2007.
IPR2013-00517 # 112, "Email from Bert Vogelstein to jre, Devin, jw2231, Jingyue Ju, Nickolas Papadopoulos and K8", dated Mar. 11, 2008.
IPR2013-00517 # 113, "Email from Bert Vogelstein to mysworld1982, dj222 and jre13", dated Mar. 3, 2008.
IPR2013-00517 # 114, "Email from Huanyan Cao to Huanyan Cao, Jerzy Olejnik, Mong Sano Marma, Waldemar Szczepanik and Wojciech Czardybon", dated Mar. 4, 2009.
IPR2013-00517 # 115, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517 # 116, "Email from Jerzy Olejnik to Stephen Buchwald and Steven Gordon", dated Aug. 10, 2007.
IPR2013-00517 # 117, "Email from Jingyue Ju to Jingue Ju and Christine Rupp", dated Jun. 5, 2008.
IPR2013-00517 # 118, "Email from msm2137 to Jingyue Ju", dated Mar. 8, 2007.
IPR2013-00517 # 119, "Email from Shiv Kumar to Jerzy Olejnik and Jinguyue Ju", dated Jul. 5, 2012.
IPR2013-00517 # 120, "Intelligent Bio-Systems, Inc., Cleavage", dated Aug. 2009.
IPR2013-00517 # 121, "Intelligent Bio-Systems, Inc., Custom Synthesis of Nucleotide Analogs", dated Aug. 1, 2012.
IPR2013-00517 # 122, "Intelligent Bio-Systems, Inc., Custom Synthesis of Nucleotide Analogs", dated My 6, 2008.
IPR2013-00517 # 123, "Intelligent Bio-Systems, Inc., Nucleotides", dated Jun. 15, 2011.
IPR2013-00517 # 124, "Inter Partes Review—Petitioner Power of Attorney", dated Apr. 4, 2014.
IPR2013-00517 # 125, "Invention Disclosure Form", dated Aug. 17, 2007.
IPR2013-00517 # 126, "Ju Lab Thesis Proposal", dated Mar. 19, 2007.
IPR2013-00517 # 127, "Ju Proposal", dated Nov. 6, 2007.
IPR2013-00517 # 128, "Ju Proposal", dated Nov. 29, 2006.
IPR2013-00517 # 129, "Lin Yu 3rd Year Research Presentation", dated May 2, 2008.
IPR2013-00517 # 130, "Note regarding Ju's Chemistry", dated May 5, 2014.
IPR2013-00517 # 131, "Research Plan", dated Feb. 2, 2006.
IPR2013-00518 # 1, "Judgment, Request for Adverse Judgment", May 6, 2014.
IPR2013-00517, "Final Written Decision", dated Feb. 11, 2015.
IPR2013-00517, "Record of Oral Hearing held Friday, Oct. 10, 2014", dated Feb. 2, 2015.
"Claims—First Auxiliary Request (annotated)", In the matter of European Patent No. 1530578 and Opposition thereto filed by Dr Christian Kilger, Oct. 27, 2015, 5 pages.
"Claims—First Auxiliary Request (clean)", In the matter of European Patent No. 1530578 and Opposition thereto filed by Dr Christian Kilger, Oct. 27, 2015, 5 pages.
"Communication from Illumina Cambridge Limited to EPO re Minutes of the Oral Proceedings held Nov. 6, 2015;", Opposition to EP1530578 by Dr. Christian Kilger, mailed Dec. 16, 2015.
"Decision rejecting the opposition (Art. 101(2) EPC)", In the matter of European Patent No. 1530578 and Opposition thereto filed by Dr Christian Kilger, Dec. 9, 2015, 23 pages.
"Declaration of Dr. Jorn Glokler", In the matter of European Patent No. 1530578 and Opposition thereto filed by Dr Christian Kilger, Nov. 2, 2015, 16 pages.
"Declaration of Dr. Michael Metzker in Support of Intelligent Bio-Systems, Inc.'s Reply to Illumina's Patent Owner Response", *Intelligent Bio-Systems, Inc.* v. *Illumina Cambridge Limited*, Case IPR2013-00517 (LMG), U.S. Pat. No. 7,566,537, Exhibit No. 1046, Jul. 28, 2014, 33 pages.
"Further Written Submissions in preparation for Oral Proceedings on Nov. 6, 2015", In the matter of European Patent No. 1530578 and Opposition thereto filed by Dr Christian Kilger, Oct. 27, 2015, 20 pages.
"Kilger Submission in reply to the summons to attend oral proceedings dated May 13, 2015", Opposition against EP1530578B1 (EP03792519.5) Patentee: Illumina Cambridge Limited, Opposition by: Dr. Christian Kilger, Oct. 1, 2015, 34 pages.
"Provision of the minutes in accordance with Rule 124(4) EPC", Minutes of the oral proceedings before the Opposition Division, EP Application No. 03792519.5 (EP Patent No. 1530578), Dec. 9, 2015, 14 pages.
"Second Declaration of Dr. Bruce Branchaud in Support of Intelligent Bio-Systems, Inc.'s Reply to Illumina's Patent Owner Response", *Intelligent Bio-Systems, Inc.* v. *Illumina Cambridge Limited*, Case IPR2013-00517 (LMG), U.S. Pat. No. 7,566,537, Exhibit No. 1031, Jul. 28, 2014, 22 pages.
"Second Declaration of Floyd Romesberg, Ph.D.", *Intelligent Bio-Systems, Inc.* v. *Illumina Cambridge Ltd.*, Case IPR2013-00266 (LMG), U.S. Pat. No. 8,158,346, Mar. 21, 2014, 20 pages.
"Video Deposition of Floyd Romesberg, Ph.D.", *Intelligent Bio-Systems, Inc.* vs. *Illumina Cambridge, Ltd.*, No. IPR2013-00517, U.S. Pat. No. 7,566,537, Jul. 8, 2014, 190 pages.
"WT 9°N can Incorporate ffG Nucleotide", Oct. 23, 2015, 1 page.
Chen, "Incorporation of 3'-Blocked dGTP by Different DNA Polymerases", Illumina, Inc. Protein Engineering Group (iPEG), Oct. 23, 2015, 8 pages.

(56) References Cited

OTHER PUBLICATIONS

Chen, "Opposition Proceedings Relating to European Patent EP1530578 (Application 03792519.2. Illumina Cambridge Limited)", Oct. 23, 2015, 5 pages.
Furman, et al., "Phosphorylation of 3'-azido-3'-deoxythymidine and selective interaction of the 5'-triphosphate with human immunodeficiency virus* reverse transcriptase", Proc. Natl. Acad. Sci. USA, vol. 83, Medical Sciences, Nov. 1986, pp. 8333-8337.
Hayakawa, et al., "Allyl and allyloxycalbonyl groups as versatile protecting groups in nucleotide synthesis", Nucleic Acids Research, Symposium Series No. 17, 1986, 97-100.
IPR2013-00128, "Substitute Declaration of Floyd Romesberg, Ph.D., In Support of Patent Owner's Motion to Amend", dated Feb. 19, 2014.
IPR2013-00517, "Decision Motion to Seal", Feb. 10, 2015.
IPR2013-00517, "Decision Motion to Seal", Jan. 29, 2015.
IPR2013-00517, "Joint Revised Motion to Seal", Feb. 5, 2015.
IPR2013-00517, "Order Conduct of the Proceeding", Apr. 16, 2015.
IPR2013-00517, "Petitioner Intelligent Bio-Systems, Inc.'s Notice of Appeal", Apr. 8, 2015.
IPR2013-0266, "Illumina Notice of Appeal in the U.S. Court of Appeals for the Federal Circuit", Nov. 26, 2014.
Zhang, Shenlong, "Development of New DNA Sequencing Approaches and Investigation of Vision-related Proteins Using Synthetic Chemistry", Columbia University, 2008.

FIG. 1
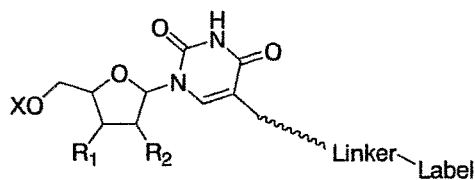
Uridine C5-linker
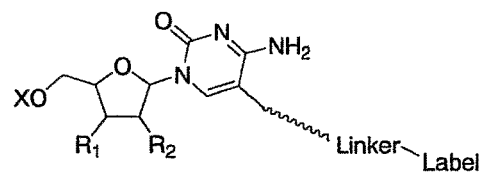
Cytidine C5-linker
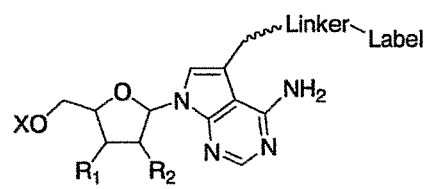
N7 Deazaadenosine C7-linker
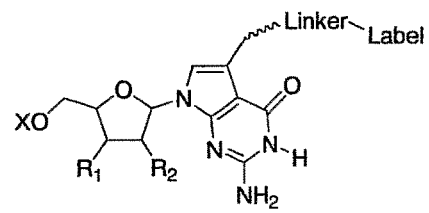
N7 Deazaguanosine C7-linker
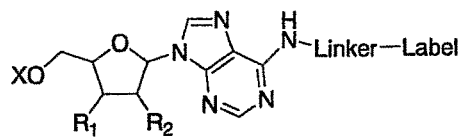
Adenosine N6-linker
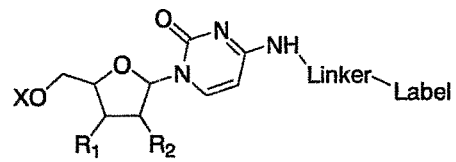
Cytidine N4-linker
where $R_1$ and $R_2$, which may be the same or different, are each selected from H, OH, or any group which can be transformed into an OH.
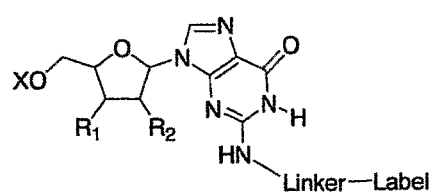
Guanosine N2-linker
X = H, phosphate, diphosphate or triphosphate FIG. 2.
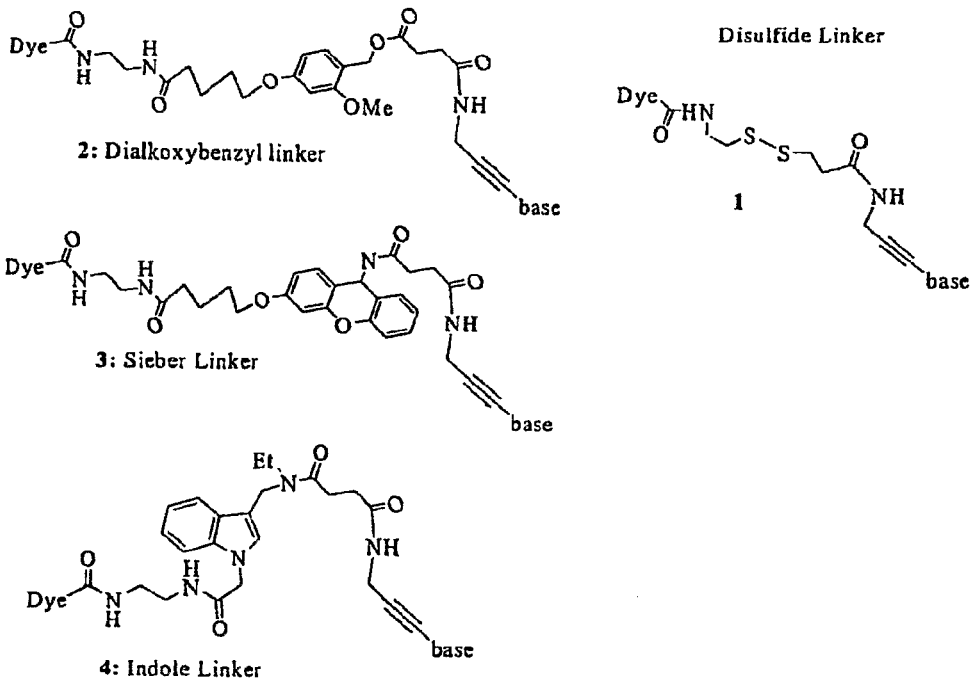
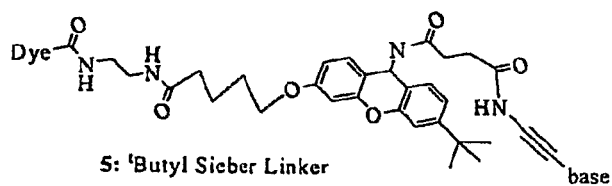
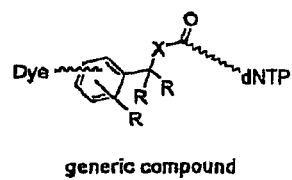
generic compound
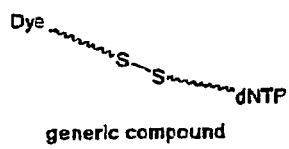
generic compound
X = O or N
R can be any substitution, including additional ring systems and systems in which the two marked R groups are linked together by further rings
the wavy bonds can symbolise anything as they are not functionally important

FIG. 3.

Label ∼∼∼Cleavable linker∼∼∼∼Base

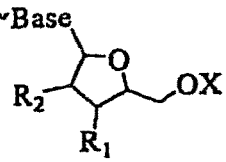

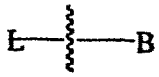

Cleavable linkers may include:

where $R_1$ and $R_2$, which may be the same or different, are each selected from H, OH, or any group which can be transformed into an OH, including a carbonyl

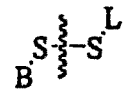

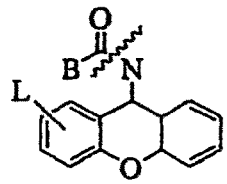

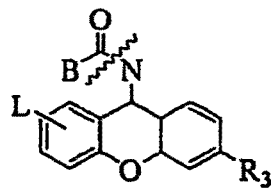

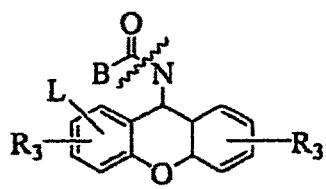

R3 represents one or more substituents independently selected from alkyl, alkoxy, amino or halogen Alternatively, cleavable linkers may be constructed from any labile functionality used on the 3'-block Klenow exo- TMR    New disulfide cleavable linker (1)
pH7.5      dUTP              +DTT Incorporation  Cleavage

AG    AG

50mM Tris-HCl pH7.5, 10mM NaCl, 0.1mM EDTA
5mM MgCl2, 2uM dNTP-fluor, 100nM SHP 5T hairpin AG oligo,
Klenow exo- (Amersham-Joyce) 10units.

New Acid cleavable Sieber linker (3)

Klenow exo- TMR
pH7.5       dUTP

AG

50mM Tris-HCl pH7.5, 10mM NaCl, 2mM DTT, 0.1mM EDTA 5mM MgCl2, 2uM dNTP-fluor, 100nM SHP 5T hairpin AG oligo, Klenow exo- (Amersham-Joyce) 10units.

t = 0, 1, 3, 5, 10

New Acid cleavable Indole linker (4)

Klenow exo- TMR
pH7.5     dUTP

AG

50mM Tris-HCl pH7.5, 10mM NaCl, 2mM DTT, 0.1mM EDTA 5mM MgCl2, 2uM dNTP-fluor, 100nM SHP 5T hairpin AG oligo, Klenow exo- (Amersham-Joyce) 10units.

t = 0, 1, 3, 5

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: 40
<223> OTHER INFORMATION: t = thymidine C6-amino

<400> SEQUENCE: 1
taccgtcgac gtcgacgctg gcgagcgtgc tgcggttttt ttaccgcagc acgctcgcca    60
gcg                                                                  63
```

LABELLED NUCLEOTIDES

This application is a continuation application of U.S. patent application Ser. No. 14/094,646, filed Dec. 2, 2013, which is a continuation application of U.S. patent application Ser. No. 13/437,772, filed Apr. 2, 2012, now abandoned; which is a continuation application of U.S. patent application Ser. No. 12/804,025, filed Jul. 13, 2010, now U.S. Pat. No. 8,158,346; which is a divisional application of U.S. patent application Ser. No. 12/283,285, filed Sep. 9, 2008, now U.S. Pat. No. 7,772,384; which is a continuation application of U.S. patent application Ser. No. 10/497,594, filed Dec. 4, 2002, now U.S. Pat. No. 7,427,673; which is a §371 national stage application of PCT/GB2002/005474, filed Dec. 4, 2002; which is a continuation-in-part application of U.S. patent application Ser. No. 10/227,131, filed Aug. 23, 2002, now U.S. Pat. No. 7,057,026, and which claims priority to United Kingdom Application No. GB0129012.1, filed Dec. 4, 2001; the contents of each of which are incorporated by reference herein in their entireties.

FIELD OF THE INVENTION

This invention relates to labelled nucleotides. In particular, this invention discloses nucleotides having a removable label and their use in polynucleotide sequencing methods.

BACKGROUND

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids, is the development of fabricated arrays of immobilised nucleic acids. These arrays consist typically of a high-density matrix of polynucleotides immobilised onto a solid support material. See, e.g., Fodor et al., *Trends Biotech.* 12:19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci. USA* 92:6379-6383, 1995).

A further development in array technology is the attachment of the polynucleotides to the solid support material to form single molecule arrays. Arrays of this type are disclosed in International Patent App. WO 00/06770. The advantage of these arrays is that reactions can be monitored at the single molecule level and information on large numbers of single molecules can be collated from a single reaction.

For DNA arrays to be useful, the sequences of the molecules must be determined. U.S. Pat. No. 5,302,509 discloses a method to sequence polynucleotides immobilised on a solid support. The method relies on the incorporation of 3'-blocked bases A, G, C and T having a different fluorescent label to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Welch et al. (*Chem. Eur. J.* 5(3):951-960, 1999) describes the synthesis of nucleotide triphosphates modified with a 3'-O-blocking group that is photolabile and fluorescent. The modified nucleotides are intended for use in DNA sequencing experiments. However, these nucleotides proved to be difficult to incorporate onto an existing polynucleotide, due to an inability to fit into the polymerase enzyme active site.

Zhu et al. (*Cytometry* 28:206-211, 1997) also discloses the use of fluorescent labels attached to a nucleotide via the base group. The labelled nucleotides are intended for use in fluorescence in situ hybridisation (FISH) experiments, where a series of incorporated labelled nucleotides is required to produce a fluorescent "bar code".

SUMMARY OF THE INVENTION

In the present invention, a nucleoside or nucleotide molecule is linked to a detectable label via a cleavable linker group attached to the base, rendering the molecule useful in techniques using labelled nucleosides or nucleotides, e.g., sequencing reactions, polynucleotide synthesis, nucleic acid amplification, nucleic acid hybridization assays, single nucleotide polymorphism studies, and other techniques using enzymes such as polymerases, reverse transcriptases, terminal transferases, or other DNA modifying enzymes. The invention is especially useful in techniques that use labelled dNTPs, such as nick translation, random primer labeling, end-labeling (e.g., with terminal deoxynucleotidyltransferase), reverse transcription, or nucleic acid amplification. The molecules of the present invention are in contrast to the prior art, where the label is attached to the ribose or deoxyribose sugar, or where the label is attached via a non-cleavable linker.

According to a first aspect of the invention, a nucleotide or nucleoside molecule, or an analog thereof, has a base that is linked to a detectable label via a cleavable linker.

The invention features a nucleotide or nucleoside molecule, having a base that is linked to a detectable label via a cleavable linker. The base can be a purine, or a pyrimidine. The base can be a deazapurine. The molecule can have a ribose or deoxyribose sugar moiety. The ribose or deoxyribose sugar can include a protecting group attached via the 2' or 3' oxygen atom. The protecting group can be removed to expose a 3'-OH. The molecule can be a deoxyribonucleotide triphosphate. The detectable label can be a fluorophore. The linker can be an acid labile linker, a photolabile linker, or can contain a disulphide linkage.

The invention also features a method of labeling a nucleic acid molecule, where the method includes incorporating into the nucleic acid molecule a nucleotide or nucleoside molecule, where the nucleotide or nucleoside molecule has a base that is linked to a detectable label via a cleavable linker. The incorporating step can be accomplished via a terminal transferase, a polymerase or a reverse transcriptase. The base can be a purine, or a pyrimidine. The base can be a deazapurine. The nucleotide or nucleoside molecule can have a ribose or deoxyribose sugar moiety. The ribose or deoxyribose sugar can include a protecting group attached via the 2' or 3' oxygen atom. The protecting group can be removed to expose a 3'-OH group. The molecule can be a deoxyribonucleotide triphosphate. The detectable label can be a fluorophore. The linker can be an acid labile linker, a photolabile linker, or can contain a disulphide linkage. The detectable label and/or the cleavable linker can be of a size sufficient to prevent the incorporation of a second nucleotide or nucleoside into the nucleic acid molecule.

In another aspect, the invention features a method for determining the sequence of a target single-stranded polynucleotide, where the method includes monitoring the sequential incorporation of complementary nucleotides, where the nucleotides each have a base that is linked to a detectable label via a cleavable linker, and where the identity of each nucleotide incorporated is determined by detection of the label linked to the base, and subsequent removal of the label.

The invention also features a method for determining the sequence of a target single-stranded polynucleotide, where the method includes: (a) providing nucleotides, where the nucleotides have a base that is linked to a detectable label via a cleavable linker, and where the detectable label linked to each type of nucleotide can be distinguished upon detection from the detectable label used for other types of nucleotides; (b) incorporating a nucleotide into the complement of the target single stranded polynucleotide; (c) detecting the label of the nucleotide of (b), thereby determining the type of nucleotide incorporated; (d) removing the label of the nucleotide of (b); and (e) optionally repeating steps (b)-(d) one or more times; thereby determining the sequence of a target single-stranded polynucleotide.

In the methods described herein, each of the nucleotides can be brought into contact with the target sequentially, with removal of non-incorporated nucleotides prior to addition of the next nucleotide, where detection and removal of the label is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label(s).

The methods can comprise a first step and a second step, where in the first step, a first composition comprising two of the four nucleotides is brought into contact with the target, and non-incorporated nucleotides are removed prior to detection and subsequent to removal of the label, and where in the second step, a second composition comprising the two nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a composition comprising one of the four nucleotides is brought into contact with the target, and non-incorporated nucleotides are removed prior to detection and subsequent to removal of the label, and where in the second step, a second composition comprising the three nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a first composition comprising three of the four nucleotides is brought into contact with the target, and non-incorporated nucleotides are removed prior to detection and subsequent to removal of the label, and where in the second step, a composition comprising the nucleotide not included in the first composition is brought into contact with the target, and non-incorporated nucleotides are removed prior to detection and subsequent to removal of the label, and where the first steps and the second step can be optionally repeated one or more times.

In a further aspect, the invention features a kit, where the kit includes: (a) individual the nucleotides, where each nucleotide has a base that is linked to a detectable label via a cleavable linker, and where the detectable label linked to each nucleotide can be distinguished upon detection from the detectable label used for other three nucleotides; and (b) packaging materials therefor. The kit can further include an enzyme and buffers appropriate for the action of the enzyme.

The nucleotides/nucleosides are suitable for use in many different DNA-based methodologies, including DNA synthesis and DNA sequencing protocols.

According to another aspect of the invention, a method for determining the sequence of a target polynucleotide comprises monitoring the sequential incorporation of complementary nucleotides, wherein the nucleotides comprise a detectable label linked to the base portion of the nucleotide via a cleavable linker, incorporation is detected by monitoring the label, and the label is removed to permit further nucleotide incorporation to occur.

DESCRIPTION OF THE DRAWINGS

FIG. 1 shows exemplary nucleotide structures useful in the invention. For each structure, X can be H, phosphate, diphosphate or triphosphate. $R_1$ and $R_2$ can be the same or different, and can be selected from H, OH, or any group which can be transformed into an OH.

FIG. 2 shows structures of linkers useful in the invention, including (1) disulfide linkers and acid labile linkers, (2) dialkoxybenzyl linkers, (3) Sieber linkers, (4) indole linkers and (5) t-butyl Sieber linkers in addition to a general definition of the linkers that may be used.

FIG. 3 shows some functional molecules useful in the invention, including some cleavable linkers. In these structures, $R_1$ and $R_2$ may be the same of different, and can be H, OH, or any group which can be transformed into an OH group, including a carbonyl. $R_3$ represents one or more substituents independently selected from alkyl, alkoxyl, amino or halogen groups. Alternatively, cleavable linkers may be constructed from any labile functionality used on the 3'-block.

FIG. 4 shows a denaturing gel showing the incorporation of the triphosphate of Example 1 using Klenow polymerase.

FIG. 5 shows a denaturing gel showing the incorporation of the triphosphate of Example 3 using Klenow polymerase.

DETAILED DESCRIPTION

Figure 6:
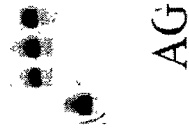
FIG. 6 shows a denaturing gel showing the incorporation of the triphosphate of Example 4 using Klenow polymerase.

The present invention relates to nucleotides and nucleosides that are modified by attachment of a label via a cleavable linker, thereby rendering the molecule useful in techniques where the labelled molecule is to interact with an enzyme, such as sequencing reactions, polynucleotide synthesis, nucleic acid amplification, nucleic acid hybridization assays, single nucleotide polymorphism studies, techniques using enzymes such as polymerase, reverse transcriptase, terminal transferase, techniques that use labelled dNTPs (e.g., nick translation, random primer labeling, end-labeling (e.g., with terminal deoxynucleotidyltransferase), reverse transcription, or nucleic acid amplification).

As is known in the art, a "nucleotide" consists of a nitrogenous base, a sugar, and one or more phosphate groups. In RNA, the sugar is a ribose, and in DNA is a deoxyribose, i.e., a sugar lacking a hydroxyl group that is present in ribose. The nitrogenous base is a derivative of purine or pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides are usually mono-, di- or triphosphates.

A "nucleoside" is structurally similar to a nucleotide, but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogs are available which do not alter the capability of the nucleotide or nucleoside to undergo Watson-Crick base pairing. "Derivative" or "analog" means a compound or molecule whose core structure is the same as, or closely resembles that of, a parent compound, but which has a chemical or physical modification, such as a different or additional side groups, which allows the derivative nucleotide or nucleoside to be linked to another molecule. For example, the base can be a deazapurine. The derivatives should be capable of undergoing Watson-Crick pairing. "Derivative" and "analog" also mean a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkylphosphonate, phosphoranilidate and phosphoramidate linkages. The analogs should be capable of undergoing Watson-Crick base pairing. "Derivative" and "analog", as used herein, may be used interchangeably, and are encompassed by the terms "nucleotide" and "nucleoside" as defined herein.

The present invention can make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the invention. For example, bi-fluorophore FRET cassettes (*Tet. Letts.* 46:8867-8871, 2000) are well known in the art and can be utilised in the present invention. Multi-fluor dendrimeric systems (*J. Amer. Chem. Soc.* 123:8101-8108, 2001) can also be used.

Although fluorescent labels are preferred, other forms of detectable labels will be apparent as useful to those of ordinary skill. For example, microparticles, including quantum dots (Empodocles, et al., *Nature* 399:126-130, 1999), gold nanoparticles (Reichert et al., *Anal. Chem.* 72:6025-6029, 2000), microbeads (Lacoste et al., *Proc. Natl. Acad. Sci USA* 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The label (or label and linker construct) can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

The invention will be further described with reference to nucleotides. However, unless indicated otherwise, the reference to nucleotides is also intended to be applicable to nucleosides. The invention will also be further described with reference to DNA, although the description will also be applicable to RNA, PNA, and other nucleic acids, unless otherwise indicated.

The modified nucleotides of the invention use a cleavable linker to attach the label to the nucleotide. The use of a cleavable linker ensures that the label can, if required, be removed after detection, avoiding any interfering signal with any labelled nucleotide incorporated subsequently.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidising agents, light, temperature, enzymes etc. Suitable linkers can be adapted from standard chemical blocking groups, as disclosed in Greene & Wuts, *Protective Groups in Organic Synthesis*, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from the nucleotide base. The cleavage site can be located at a position on the linker that ensures that part of the linker remains attached to the nucleotide base after cleavage.

The linker can be attached at any position on the nucleotide base provided that Watson-Crick base pairing can still be carried out. In the context of purine bases, it is preferred if the linker is attached via the 7 position of the purine or the preferred deazapurine analogue, via an 8-modified purine, via an N-6 modified adenosine or an N-2 modified guanine. For pyrimidines, attachment is preferably via the 5 position on cytidine, thymidine or uracil and the N-4 position on cytosine. Suitable nucleotide structures are shown in FIG. 1. For each structure in FIG. 1, X can be H, phosphate, diphosphate or triphosphate. $R_1$ and $R_2$ can be the same or different, and can be selected from H, OH, or any group which can be transformed into an OH, including, but not limited to, a carbonyl.

Suitable linkers are shown generally in FIG. 2 and include, but are not limited to, disulfide linkers (1), acid labile linkers (2, 3, 4 and 5; including dialkoxybenzyl linkers (e.g., 2), Sieber linkers (e.g., 3), indole linkers (e.g., 4), t-butyl Sieber linkers (e.g., 5)), electrophilically cleavable linkers, nucleophilically cleavable linkers, photocleavable linkers, cleavage under reductive conditions, oxidative conditions, cleavage via use of safety-catch linkers, and cleavage by elimination mechanisms.

A. Electrophilically Cleaved Linkers.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system (e.g., as is shown in FIG. 3 as O—C($R_4$) ($R_5$)—O—$R_6$.

The use of thiophilic metals, such as nickel, silver or mercury, in the cleavage of thioacetal or other sulphur-containing protecting groups can also be considered for the preparation of suitable linker molecules.

B. Nucleophilically Cleaved Linkers.

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers.

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenyl compounds and nitroveratryl compounds. Linkers based on benzoin chemistry can also be used (Lee at al., *J. Org. Chem.* 64:3454-3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulphide bond reduction is also known in the art.

E. Cleavage Under Oxidative Conditions

Oxidation-based approaches are well known in the art. These include oxidation of p-alkoxybenzyl groups and the oxidation of sulphur and selenium linkers. The use of aqueous iodine to cleave disulphides and other sulphur or selenium-based linkers is also within the scope of the invention.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., *J. Org. Chem.* 62:5165-5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

As well as the cleavage site, the linker can comprise a spacer unit. The spacer distances the nucleotide base from the cleavage site or label. The length of the linker is unimportant provided that the label is held a sufficient distance from the nucleotide so as not to interfere with any interaction between the nucleotide and an enzyme.

The modified nucleotides can also comprise additional groups or modifications to the sugar group. For example, a dideoxyribose derivative, lacking two oxygens on the ribose ring structure (at the 2' and 3' positions), can be prepared and used as a block to further nucleotide incorporation on a growing oligonucleotide strand. The protecting group is intended to prevent nucleotide incorporation onto a nascent polynucleotide strand, and can be removed under defined conditions to allow polymerisation to occur. In contrast to the prior art, there is no detectable label attached at the ribose 3' position. This ensures that steric hindrance with the polymerase enzyme is reduced, while still allowing control of incorporation using the protecting group.

The skilled person will appreciate how to attach a suitable protecting group to the ribose ring to block interactions with the 3'-OH. The protecting group can be attached directly at the 3' position, or can be attached at the 2' position (the protecting group being of sufficient size or charge to block interactions at the 3' position). Alternatively, the protecting group can be attached at both the 3' and 2' positions, and can be cleaved to expose the 3'OH group.

Suitable protecting groups will be apparent to the skilled person, and can be formed' from any suitable protecting group disclosed in Green and Wuts, supra. The protecting group should be removable (or modifiable) to produce a 3' OH group. The process used to obtain the 3' OH group can be any suitable chemical or enzymic reaction.

The labile linker may consist of functionality cleavable under identical conditions to the block. This will make the deprotection process more efficient as only a single treatment will be required to cleave both the label and the block. Thus the linker may contain functional groups as described in FIG. 3, which could be cleaved with the hydroxyl functionality on either the residual nucleoside or the removed label. The linker may also consist of entirely different chemical functionality that happens to be labile to the conditions used to cleave the block.

The term "alkyl" covers both straight chain and branched chain alkyl groups. Unless the context indicates otherwise, the term "alkyl" refers to groups having 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Examples of alkenyl groups include, but are not limited to, ethenyl (vinyl), 1-propenyl, 2-propenyl (allyl), isopropenyl, butenyl, buta-1,4-dienyl, pentenyl, and hexenyl.

Examples of cycloalkenyl groups include, but are not limited to, cyclopropenyl, cyclobutenyl, cyclopentenyl, cyclopentadienyl and cyclohexenyl.

The term alkoxy refers to $C_{1-6}$ alkoxy unless otherwise indicated: —OR, wherein R is a $C_{1-6}$alkyl group. Examples of $C_{1-6}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

The term amino refers to groups of type $NR^1R^2$, wherein $R^1$ and $R^2$ are independently selected from hydrogen, a $C_{1-6}$ alkyl group (also referred to as $C_{1-6}$ alkylamino or di-$C_{1-6}$alkylamino).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotides.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the labelled nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or vent polymerase. A polymerase engineered to have specific properties can also be used.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material.

The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International App. No. WO 00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. The conditions necessary for polymerisation to occur will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide, may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 µm. For a description of scanning near-field optical microscopy, see Moyer at al., *Laser Focus World* 29:10, 1993. Suitable apparatus' used for imaging polynucleotide arrays are known and the technical set-up will be apparent to the skilled person.

After detection, the label may be removed using suitable conditions that cleave the linker.

The use of the modified nucleotides is not limited to DNA sequencing techniques, and other techniques, including polynucleotide synthesis, DNA hybridisation assays and single nucleotide polymorphism studies, may also be carried out using nucleotides of the invention. Any technique that involves the interaction between a nucleotide and an enzyme may make use of the molecules of the invention. For example, the molecule may be used as a substrate for a reverse transcriptase or terminal transferase enzyme.

Suitable structures are described in the following Examples and are shown in the accompanying drawings.

EXAMPLES

Example 1

Synthesis of Disulfide Linker

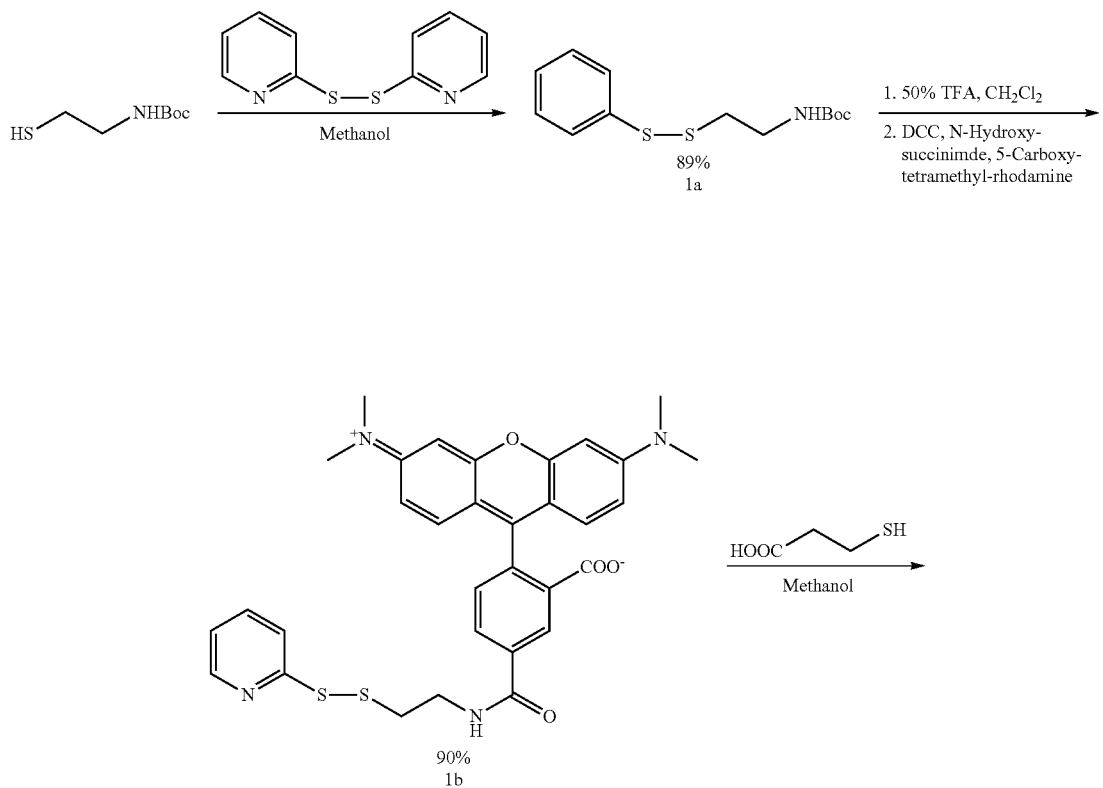

-continued

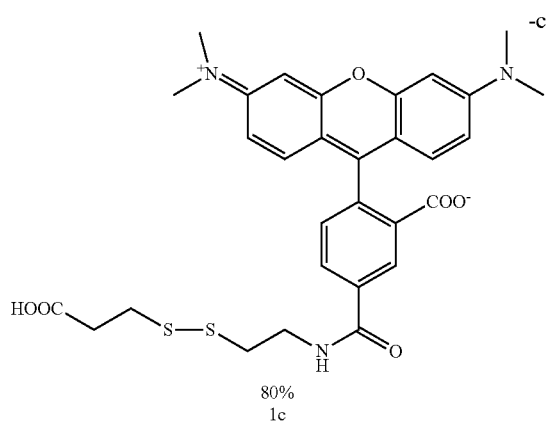

80%
1c

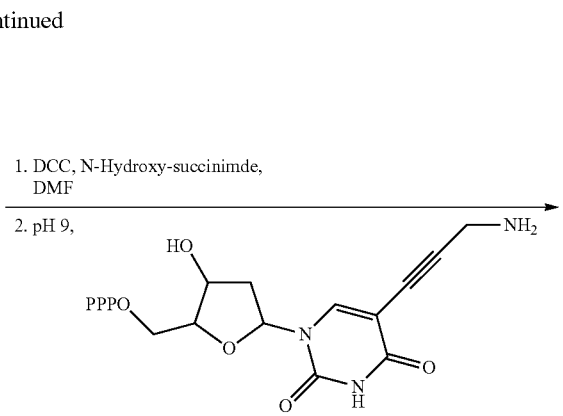

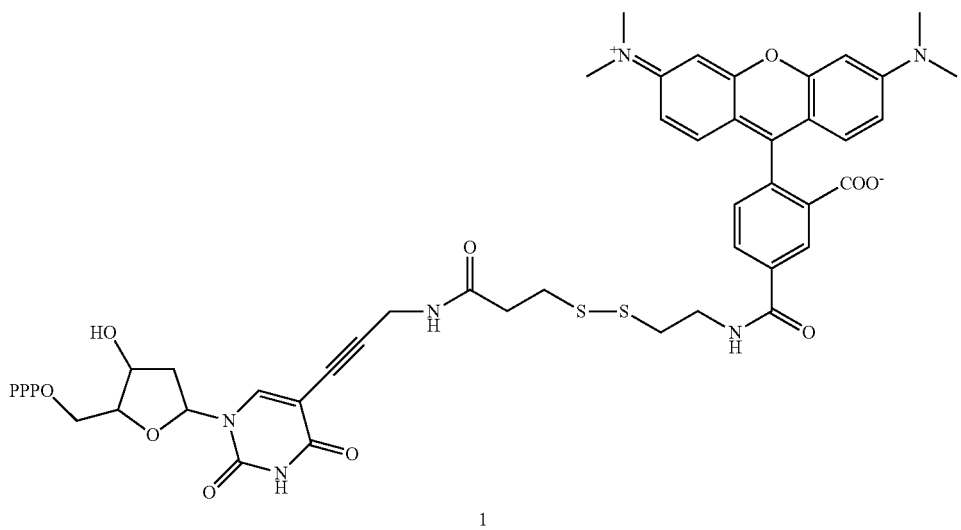

1

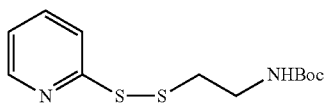

1a tButyl-N-(2-mercaptoethyl) carbamate (3 mmol, 0.5 mL) was added dropwise to a solution of 1.32 g (6.0 mmol) aldrithiol in 15 mL MeOH. After 1.5 h the reaction had gone to completion and the solvent was evaporated. The crude product was purified by chromatography on silica with ethyl acetate:petroleum ether (1:4). Product 1a was obtained as a slightly yellow oil (0.76 g, 2.67 mmol, 89%). $^1$H NMR (500 Mhz, D$_6$-DMSO): d=1.38 (s, 9H, tBu), 2.88 (t, J=6.6 Hz, 2H, SCH$_2$) 3.20 (q, J=6.6 Hz, 2H, C$\underline{H}_2$NH), 7.02 (bs, 1H, NH), 7.24 (ddd, j=7.3 Hz, J=4.9 Hz, J=1.0 Hz, 1H, H-5), 7.77 (dt, J=8.1 Hz, J=1.0 Hz, 1H, H-3), 7.82 (ddd, J=8.1 Hz, J=7.4 Hz, J=1.8 Hz, 1H, H-4), 8.46 (ddd, J=4.9 Hz, J=1.8 Hz, J=1.0 Hz, 1H, H-6).

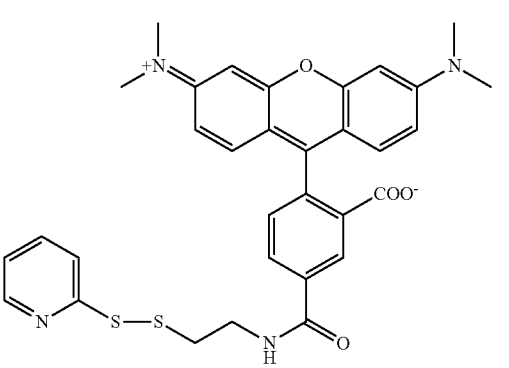

1b

To deprotect the amine of 1a, 17 mg of 1a (60 µmol) was dissolved in a mixture of 0.5 mL DCM and 0.5 mL trifluoracetic acid. This mixture was stirred for 2.5 h at room temperature and then the solvents were removed under reduced pressure. The residue was three times redissolved in 2 mL DCM and evaporated to dryness. The deprotected product was dried under high vacuum for 3 h and then dissolved in 1 mL dry DMF. It was assumed that the deprotection had gone to completion.

To a solution of 15 mg 5-carboxy tetra methyl rhodamine (35 µmol) in 2 mL DMF were added 8.0 mg N-hydroxy succinimide (70 µmol) and 7.8 mg DCC (38 µmol). The mixture was stirred for 6 h in the dark. Then 22 µl DIPEA (126 µmol) and the solution of deprotected 1a in 1 mL DMF were added. After stirring the reaction mixture overnight in the dark, the solvent was removed under reduced pressure. The residue was dissolved in DCM and washed with saturated NaCl solution. After drying over MgSO₄ the crude mixture was purified on silica with CHCl₃:MeOH (3:1) as solvent. 1b was isolated as a dark red solid in 90% yield (19.2 mg, 31.4 µmol). $^1$H NMR (500 MHz, D$_6$-DMSO): δ=3.09 (t, J=6.7 Hz, 2H, SCH$_2$), 3.63 (q, J=6.2 Hz, 2H, CH$_2$NH), 6.48-6.53 (m, 6H, H-Anthracene), 7.23-7.26 [m, 1H, H-5 (pyridine)], 7.32 (d, J=7.9 Hz, 1 Hz, H-3), 7.81-7.82 [m, 2H, H-3+H-4 (pyridine)], 8.21 (d, J=7.9 Hz, 1H, H-4), 8.43 (s, 1H, H-6), 8.47 [dt, J=4.7 Hz, J=1.3 Hz, 1H, H-6 (pyridine)], 9.03 (t, J=5.2 Hz, 1H, NH).

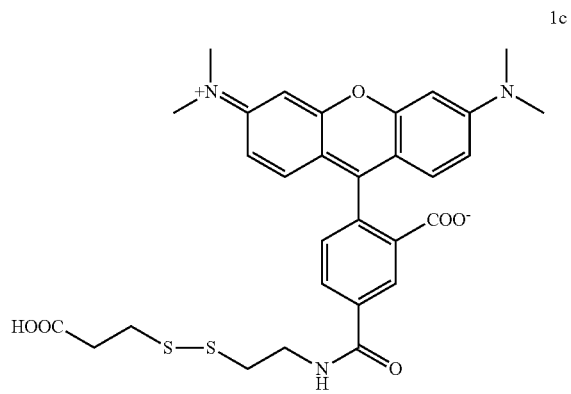

1c

Mercaptopropionic acid (20.6 µmol, 1.8 ml) was added to a solution of 19.6 mg. 1b (32.7 µmol) in 2 mL MeOH. The mixture was stirred for 2.5 h in the dark. The solvent was removed under reduced pressure. The crude product was purified by chromatography on silica with CHCl₃:MeOH:AcOH 15:1:0.5 as the solvent mixture. 15.5 mg (26 µmol, 80%) dark red crystals 1c could be isolated. $^1$H NMR (500 MHz, D$_2$O): δ=2.53 (t, J=7.0 Hz, 2H, CH$_2$COOH), 2.88 (t, J=7.0 Hz, 2H, CH$_2$CH$_2$COOH), 2.96-2.99 (m, 2H, CH$_2$CH$_2$NH), 3.73 (t, J=6.3 Hz, 2H, CH$_2$NH), 6.53 (d, J=2.4 Hz, 2H, H-Anthracene), 6.81 (dd, J=9.5 Hz, J=4.5 Hz, 2H, H-Anthracene), 7.12 (d, J=9.5 Hz, 2H, H-Anthracene), 7.48 (d, J=7.9 Hz, 1H, H-3), 7.95 (dd, J=8.1 Hz, J=1.9 Hz, 1H, H-2) 8.13 (d, J=1.9 Hz, 1H, H-1). +ve electro spray (C$_{30}$H$_{31}$N$_3$O$_6$S$_2$): expected 593.17. found 594.3 [M+H], 616.2 [M+Na].

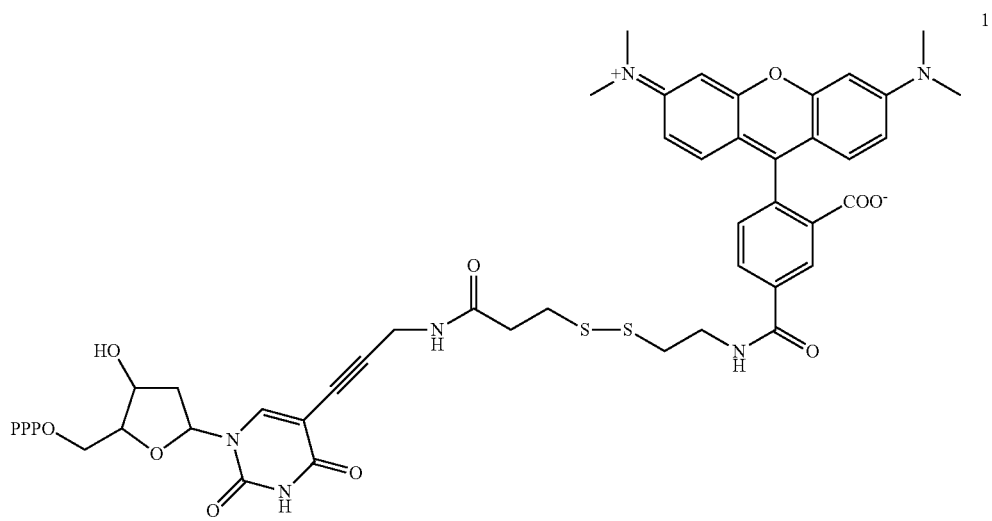

1

To a solution of 25.8 mg 1c (43.4 µmol) in 3 mL DMF (dry) were added 9.9 mg N-hydroxy succinimide (86.8 µmol) and 9.7 mg DCC (47.1 µmol). The mixture was stirred in the dark for 5 h at room temperature and then put in the fridge overnight. The mixture was filtered through a plug of cotton wool in a new flask and to this was added a solution of 865 µl propargylamino dUTP (14.7 µmol, 17 µmol in 1 mL H$_2$O) and, 3 mL sodium borate buffer (0.1 M solution, pH 9). The mixture was stirred overnight. After removal of solvents the residue was dissolved in as little water as possible and purified by HPLC. A Zorbax C18 column was used with 0.1 M triethyl ammonium bicarbonate (TEAB) and acetonitrile as buffers. $^{31}$P NMR (400 MHz, D$_2$O): δ=−4.73 (d), −9.93 (d), 19.03 (t). −ve electro spray (C$_{42}$H$_{47}$N$_6$O$_{19}$P$_3$S$_2$ assuming 4H$^+$ counter ions): expected 1096.16. found 1092.9. UV in Water: λ$_{(max)}$=555 nm λ$_{(555)}$= 0.885 (c=0.036 µmol).

Triphosphate (1) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCg-AgCgTgCTgCggTTTTT (C6-amino) TTACCgCAg-CACgCTCgCCAgCg; SEQ ID NO:1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (disulfide linker gel, FIG. 4). A second set of lanes is shown in which the material is exposed to DTT after the incorporation. A different band shift can be seen which shows removal of the dye from the DNA construct, thus a cycle of polymerase incorporation and cleavage has been shown using this disulfide compound.

Example 2

Synthesis of TMR-Sieber Linker Free Acid

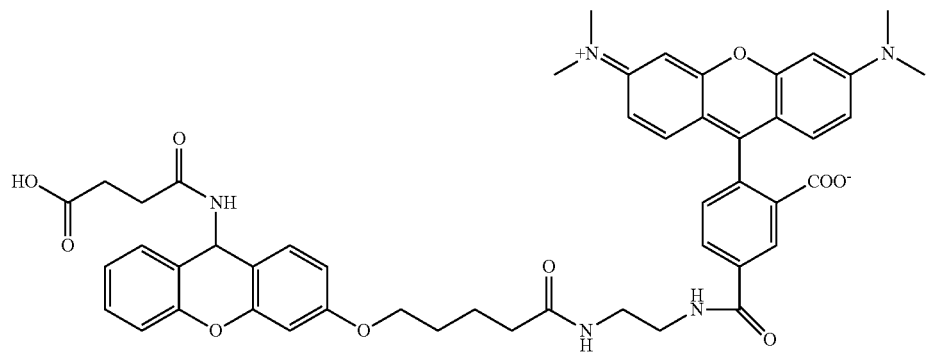

5-[-9-[9-(fluorenyl-methyloxycarbonyl)amino]xanthen-3-yl]valeric acid, (42.8 mg, 80 µmol) was stirred at room temperature with disuccinimidyl carbonate (22.5 mg, 88 µmol) and N,N-dimethyl aminopyridine (10.8 mg, 88 µmol) in DMF. After 5 minutes, mono-5-carboxy TMR ethylene diamine (198.9 mg, 40 µmol) was added followed by DIPEA (13.9 µl, 80 µmol). The reaction was stirred at room temperature. After 2 hrs, the reaction mixture was diluted with dichloromethane (100 mL) and the resulting solution was extracted with 1 M aqueous potassium dihydrogen phosphate (50 mL). The DCM layer was separated and evaporated under reduced pressure. The residue was purified by a short column chromatography. The fractions eluting with 40% methanol in chloroform were collected and evaporated under reduced pressure. The residue was then dissolved in dry DMF (1 mL) and N-(2-mercaptoethyl)aminomethyl polystyrene (200 mg, 400 µmol) and DBU (12 µl, 80 µmol). After 10 minutes at room temperature, the resins were filtered off and rinsed with dry DMF (1 mL). All the filtrates were combined and then added to a solution of succinic anhydride (80 mg, 800 µmol), DIPEA (139 µl, 800 µmol) and DMAP (9.8 mg, 80 µmol) in DMF (1 mL). The reaction mixture was then stirred at room temperature. After overnight (16 hrs), all the solvents were evaporated under reduced pressure and the residue was purified by a short column chromatography. The title compound eluted with 30% methanol in chloroform obtained as purple powders (22 mg, overall yield 63%). $^1$HNMR [$D_6$-DMSO]: 8.82 (1H, t, J 5.4, ex.), 8.75 (1H, d, J 8.9, ex.), 8.42 (1H, d, J 1.5), 8.20 (1H, dd, J 8.0 and 1.5), 7.95 (1H, t, J 5.9, ex.), 7.34 (1H, d, J 7.3), 7.30-7.27 (2H, m), 7.21 (1H, d, J 8.5), 7.16-7.07 (2H, m), 6.68 (1H, dd, J 8.8 and 2.5), 6.65 (1H, d, J 2.4), 6.49-6.43 (6H, m), 6.18 (1H, d, J 5.6), 3.95 (1H, t, J 5.9), 3.39-3.36 (2H, m), 3.30-3.27 (2H, m), 2.92 (12H, s), 2.37-2.33 (2H, m), 2.14 (2H, t, J 7.2) and 1.70-1.62 (4H, m). MS[(ES(+)], m/z 868.5 (MH$^+$).

Example 3

Synthesis of TMR-Sieber Linker-dUTP(3)

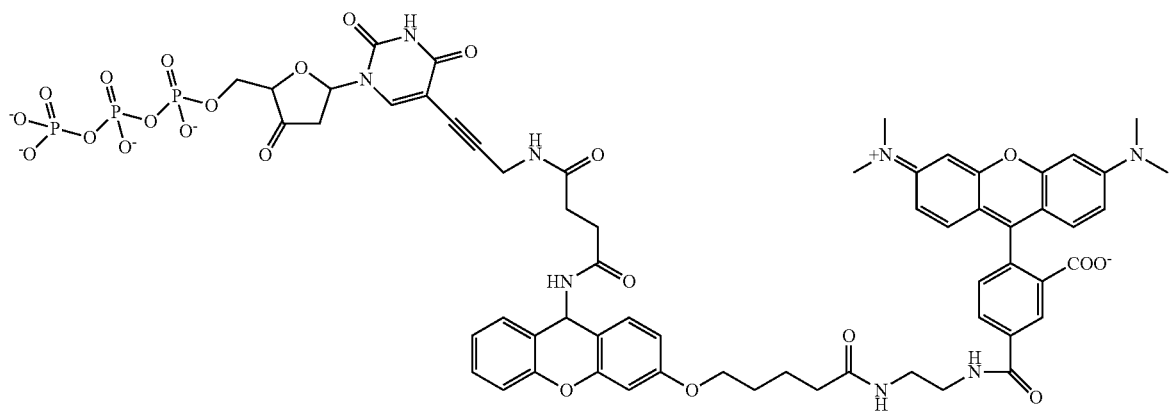

TMR-sieber linker free acid (4.34 mg, 5 µmol) was stirred with disuccinimidyl carbonate (1.74 mg, 7.5 µmol) and N,N-dimethyl aminopyridine (0.92 mg, 7.5 µmol) in DMF (1 mL) at room temperature. After 10 minutes, all the reaction mixture was added to tetra-(tri-butylammonium) salt of 5-(3-aminopropynyl)-2'-deoxyuridine-5'-triphosphate (10 µmol). The reaction was stirred at room temperature for 4 hrs and stored in the fridge overnight. The reaction mixture was then diluted with chilled water (10 mL) and all the resulting solution was applied onto a short column of DEAE A-25. The column was initially eluted with 0.1 M TEAB buffer and then 0.7 M TEAB buffer. The 0.7 M TEAB eluents were collected and evaporated under reduced pressure. The residue was co-evaporated with MeOH (2×10 mL) and then purified by preparative HPLC. The title compound at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (Sieber linker gel, FIG. 5).

Example 4

Synthesis of TMR-Indole Linker-dUTP (4)

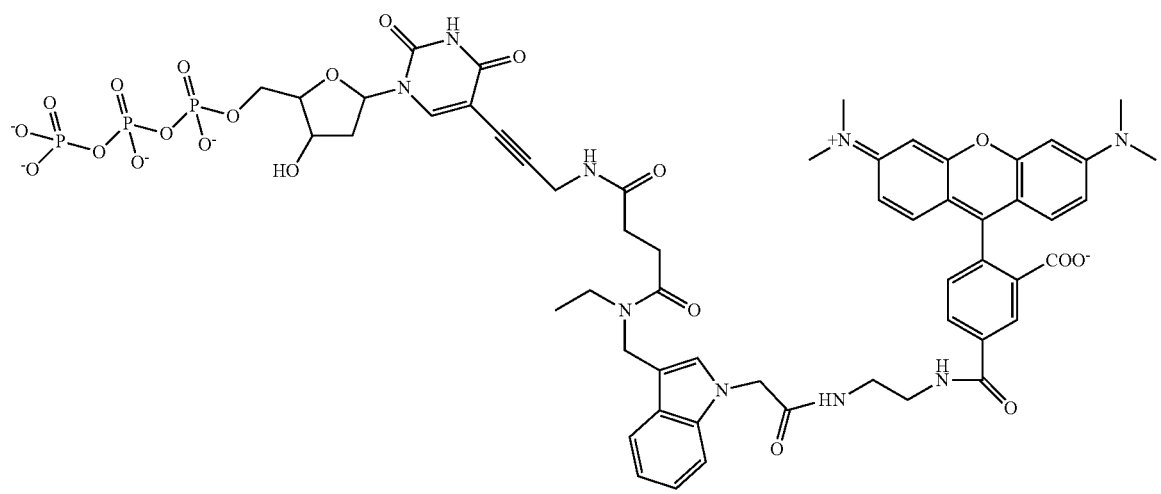

was obtained as triethylammonium salt in 31% yield (based on the quantification of TMR at 555 nm in water (pH 7)). $^1$HNMR in $D_2O$ indicated two diastereoisomers, due to the sieber linker moiety and there were approximately three triethylammonium count ions. $^1$HNMR [$D_2O$]: 8.18 (1H, m), 8.06 (1H, m), 7.76 (0.55H, s), 7.74 (0.45H, s), 7.36-7.09 (5H, m), 6.89-6.72 (3H, m), 6.59-6.37 (5H, m), 6.12 (0.55H, t, J 6.6), 6.05 (0.45H, t, J 6.6), 5.99 (0.45H, d, J 2.5), 5.91 (1.1H, m), 5.88 (0.45H, s), 4.49 (0.55H, m), 4.43 (0.45H, m), 4.00-3.35 (9H, m), 3.30-2.95 (32H, m), 2.65-2.52 (4H, m), 2.25-2.05 (4H, m), 1.62-1.42 (4H, m) and 1.23 (27H, t, J 7.3). $^{31}$P [$D_2O$]: −9.91 ($^\gamma$P, d, J 19.2), [−11.08 ("P, d, J 20.1) and −11.30 ("P, d, J 20.1), due to two diastereoisomers] and −22.57 ($^\beta$P, m). MS[(ES(−)], m/z 1369.1 (M$^-$).

Triphosphate (3) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp. Arlington Heights, Ill., USA). The DNA templates were self-complementary hairpins (5'-TACCgTCgACgTCgACgCTggCg-AgCgTgCTgCggTTTTT (C6-amino) TTACCgCAg-CACgCTCgCCAgCg; SEQ ID NO:1). The reaction was performed in 100 µL volume at 37° C. with timepoints taken Triphosphate (4) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCg-AgCgTgCTgCggTTTTT(C6-amino)TTACCgCAg-CACgCTCgCCAgCg; SEQ ID NO:1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (indole linker gel, FIG. 6).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for determining the sequence of a target single-stranded polynucleotide, comprising monitoring the sequential incorporation of complementary nucleotides,
wherein the nucleotides each have a base that is linked to a detectable label vial a cleavable linker comprising an azido group, wherein each of the nucleotides has a ribose or deoxyribose sugar moiety and the ribose or deoxyribose sugar moiety comprises an azido protecting group attached via the 2' or 3' oxygen atom, and
wherein the identity of each nucleotide incorporated is determined by detection of the label linked to the base, and subsequent removal of the label and the protecting group under a single set of conditions.

2. The method according to claim 1, further comprising the steps of
(a) providing said nucleotides;
and wherein said monitoring comprises
(b) incorporating a nucleotide into the complement of the target single stranded polynucleotide;
(c) detecting the label of the nucleotide of (b), thereby determining the type of nucleotide incorporated;
(d) removing the label of the nucleotide of (b); and
(e) optionally repeating steps (b)-(d) one or more times; thereby determining the sequence of a target single-stranded polynucleotide.

3. The method according to claim 1,
wherein each of the nucleotides are brought into contact with the target sequentially, with removal of non-incorporated nucleotides prior to addition of the next nucleotide, and
wherein detection and removal of the label is carried out either after addition of each nucleotide, or after addition of all four nucleotides.

4. The method according to claim 1, wherein each of the nucleotides are brought into contact with the target together simultaneously, and non-incorporated nucleotides are removed prior to detection and subsequent to removal of the label.

5. The method according to claim 1, comprising a first step and a second step,
wherein in the first step, a first composition comprising two of the four nucleotides is brought into contact with the target, and non-incorporated nucleotides are removed prior to detection and subsequent to removal of the label, and
wherein in the second step, a second composition comprising the two nucleotides not included in the first composition is brought into contact with the target, and non-incorporated nucleotides are removed prior to detection and subsequent to removal of the label,
and wherein the first step and the second step are optionally repeated one or more times.

6. The method according to claim 1, comprising a first step and a second step,
wherein in the first step, a first composition comprising one of the four nucleotides is brought into contact with the target, and non-incorporated nucleotides are removed prior to detection and subsequent to removal of the label, and
wherein in the second step, a second composition comprising the three nucleotides not included in the first composition is brought into contact with the target, and non-incorporated nucleotides are removed prior to detection and subsequent to removal of the label,
and wherein the first step and the second step are optionally repeated one or more times.

7. The method according to claim 1, comprising a first step and a second step,
wherein in the first step, a first composition comprising three of the four nucleotides is brought into contact with the target, and non-incorporated nucleotides are removed prior to detection and subsequent to removal of the label, and
wherein in the second step, a second composition comprising the nucleotide not included in the first composition is brought into contact with the target, and non-incorporated nucleotides are removed prior to detection and subsequent to removal of the label,
and wherein the first step and the second step are optionally repeated one or more times.

8. The method according to claim 1, wherein each of the nucleotides has a base that is linked to a detectable label via a cleavable linker, wherein the cleavable linker comprises a protected hydroxyl functionality.

9. The method according to claim 1, wherein cleavage of the cleavable linker produces a hydroxyl group attached to the base.

10. The method according to claim 1, wherein cleavage of the cleavable linker produces a hydroxyl group attached to the detectable label.

11. The method according to claim 1, wherein each of the nucleotides is a deoxyribonucleotide triphosphate.

12. The method according to claim 1, wherein the detectable label is a fluorophore.

13. The method according to claim 1, wherein the detectable label and/or cleavable linker is of sufficient size to limit the incorporation of further nucleotides into a nucleic acid template strand.

14. The method according to claim 1, wherein the target single-stranded polynucleotide is immobilised on a solid support.

15. The method according to claim 14, wherein the solid support is a bead or microsphere.

16. The method according to claim 14, wherein the solid support is a glass slide.

* * * * *

UNITED STATES PATENT AND TRADEMARK OFFICE
CERTIFICATE OF CORRECTION

PATENT NO. : 9,605,310 B2
APPLICATION NO. : 14/821566
DATED : March 28, 2017
INVENTOR(S) : Balasubramanian et al.

It is certified that error appears in the above-identified patent and that said Letters Patent is hereby corrected as shown below:

On the Title Page

Item (72), (Inventors) at Lines 3-4, Change "Nr. Safron Walden (GB)" for Xiaohai Liu to --Nr. Saffron Walden (GB)--.

In the Specification

In Column 1 at Line 13 (approx.), Change "Dec. 4, 2002," to --Mar. 28, 2005,--.

In Column 6 at Line 11 (approx.), Change "Sci" to --Sci.--.

In Column 7 at Line 63 (approx.), Change "O-nitrobenyl" to --O-nitrobenzyl--.

In Column 7 at Line 66 (approx.), Change "Lee at al." to --Lee et al.--.

In Column 8 at Line 66 (approx.), Change "formed'" to --formed--.

In Column 9 at Line 51 (approx.), Change "di-$C_{1-6}$alkylamino)." to --di-$C_{1-6}$ alkylamino).--.

In Column 11 at Line 4, Change "polynucleotide," to --polynucleotide--.

In Column 12 at Line 9 (approx.), Change "Moyer at al." to --Moyer et al.--.

In Column 12 at Line 10 (approx.), Change "apparatus'" to --apparatus--.

In Column 14 at Lines 63-64, Change "trifluoracetic" to --trifluoroacetic--.

In Column 15 at Line 65, Change "mg." to --mg--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,605,310 B2

In Column 16 at Line 7 (approx.), Change "J='4.5 Hz" to --J=4.5 Hz--.

In Column 16 at Line 12 (approx.), Change "593.17." to --593.17;--.

In Column 16 at Line 44, Change "and," to --and--.

In Column 16 at Line 52, Change "1096.16." to --1096.16;--.

In Column 16 at Line 52, Change "$\lambda_{(555)}$" to --$A_{(555)}$--.

In Column 17 at Line 44-63 (approx.), Change

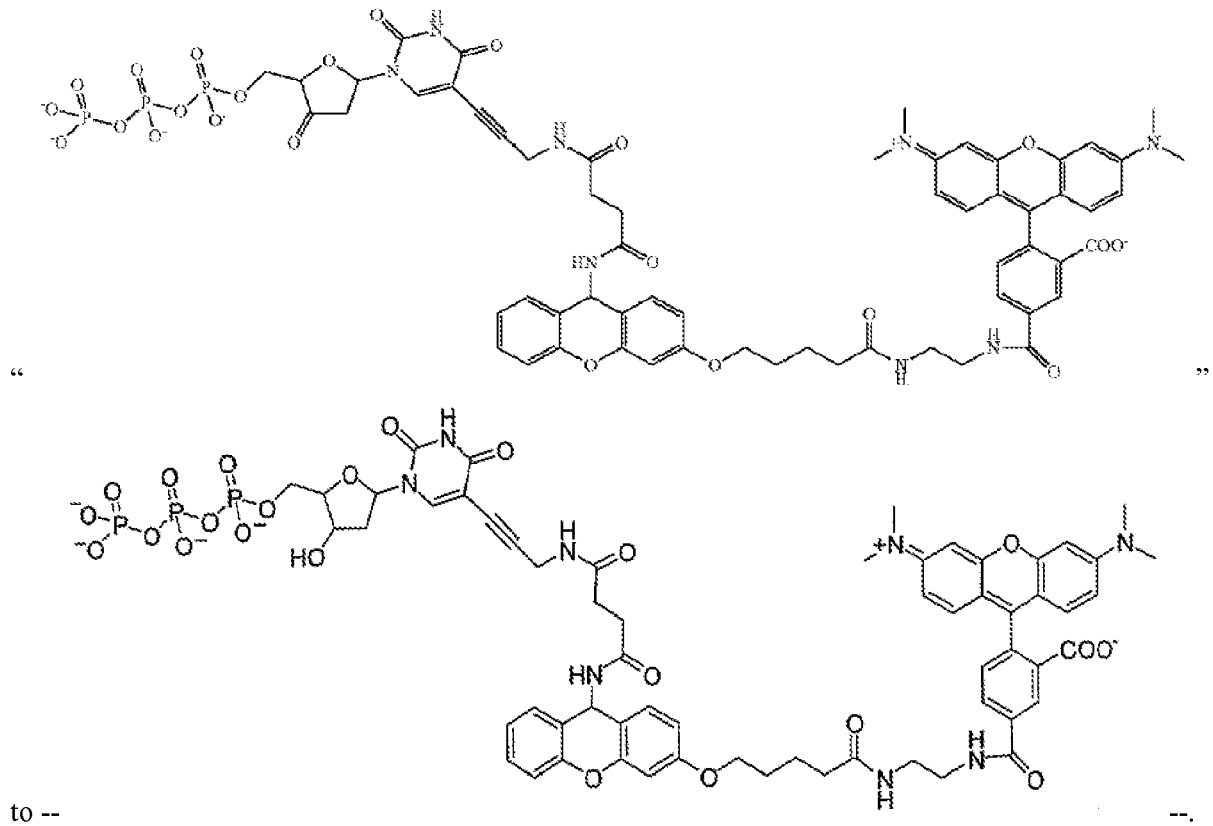

to -- --.

In the Claims

In Column 21 at Line 26 (approx.), In Claim 1, change "vial" to --via--.